United States Patent
Kim et al.

(10) Patent No.: US 9,441,017 B2
(45) Date of Patent: Sep. 13, 2016

(54) WATER-SOLUBLE POLYPEPTIDES COMPRISED OF REPEAT MODULES, METHOD FOR PREPARING THE SAME AND METHOD FOR A TARGET-SPECIFIC POLYPEPTIDE AND ANALYSIS OF BIOLOGICAL ACTIVITY THEREOF

(75) Inventors: Hak Sung Kim, Daejeon (KR); Dong Sup Kim, Daejeon (KR); Sang Chul Lee, Daejeon (KR); Byung Chul Lee, Seoul (KR); Ji Eun Han, Daejeon (KR); Joong Jae Lee, Daejeon (KR); Keun Wan Park, Daejeon (KR); Seung Pyo Hong, Daejeon (KR)

(73) Assignee: KOREA ADVANCED INSTITUTE OF SCIENCE AND TECHNOLOGY, Daejeon (KR)

( * ) Notice: Subject to any disclaimer, the term of this patent is extended or adjusted under 35 U.S.C. 154(b) by 0 days.

(21) Appl. No.: 14/005,536

(22) PCT Filed: Mar. 22, 2012

(86) PCT No.: PCT/KR2012/002094
§ 371 (c)(1),
(2), (4) Date: Nov. 22, 2013

(87) PCT Pub. No.: WO2012/128580
PCT Pub. Date: Sep. 27, 2012

(65) Prior Publication Data
US 2014/0088292 A1 Mar. 27, 2014

(30) Foreign Application Priority Data
Mar. 22, 2011 (KR) .................. 10-2011-0025446

(51) Int. Cl.
C07K 14/195 (2006.01)
C07K 14/705 (2006.01)
G01N 33/50 (2006.01)
G06F 19/16 (2011.01)
C12Q 1/68 (2006.01)
C07K 14/46 (2006.01)
C12N 15/70 (2006.01)

(52) U.S. Cl.
CPC ............ *C07K 14/195* (2013.01); *C07K 14/46* (2013.01); *C07K 14/705* (2013.01); *C12N 15/70* (2013.01); *C12Q 1/6897* (2013.01); *G01N 33/5023* (2013.01); *G06F 19/16* (2013.01); *C07K 2319/35* (2013.01); *C07K 2319/70* (2013.01)

(58) Field of Classification Search
None
See application file for complete search history.

(56) References Cited

FOREIGN PATENT DOCUMENTS

KR   10-2011-0099600 A   9/2011
KR   1020110099600 A     9/2011
WO   WO 2009156171 A1 * 12/2009

OTHER PUBLICATIONS

Bowie et al. (Science, 1990, 247:1306-1310).*
Burgess et al. (J. Cell Biol. 111:2129-2138, 1990).*
Lazar et al. (Mol. Cell. Biol., 8:1247-1252, 1988).*
Bork (Genome Research, 2000, 10:398-400).*
Papaneophytou et al (Protein Expression and Purification 94 (2014) 22-32).*
Habibi et al. BMC Bioinformatics 2014, 15:134.*
Baabur et al., "Artificial Repeat Protein Receptors," Journal of Peptide Science (2008) vol. 14, No. 8, suppl. S, p. 108.
Courtemanche et al., "The Leucine-Rich Repeat Domain of Internalin B Folds along a Polarized N-Terminal Pathway," Structure (2008) 16: 705-714.
Herrin et al., "Structure and specificity of lamprey monoclonal antibodies," Proceedings of the National Academy of Sciences USA (2008) 105(6): 2040-2045.
Lee et al., "Design of a binding scaffold based on variable lymphocyte receptors of jawless vertebrates by module engineering," Proceedings of the National Academy of Sciences USA (2012) 109(9): 3299-3304, published online Feb. 10, 2012.
Wezner-Ptasinska et al., "Design and characteristics of a stable protein scaffold for specific binding based on variable lymphocyte receptor sequences," Biochimica et Biophysica Acta (2011) 1814(9): 1140-1145.
Bryce, Andrew, International Search Report and Written Opinion, PCT/KR2012/002094, Australian Patent Office, Jun. 26, 2012.
Akashi et al., "Lipopolysaccharide Interaction with Cell Surface Toll-like Receptor 4-MD-2: Higher Affinity than That with MD-2 or CD14", The Journal of Experimental Medicine, vol. 198, No. 7, Oct. 6, 2003, pp. 1035-1042.
Baabur et al., "Artifical Repeat Protein Receptors", Journal of Peptide Science (2008), vol. 14, No. 8, Suppl. S, p. 108.
Brandl et al., "A designed TLR4/MD-2 complex to capture LPS", Journal of Endotoxin Research, vol. 11, No. 4, 2005, pp. 197-206.
Courtemanche et al., "The leucine-rich repeat domain of Internalin B folds along a polarized N-terminal pathway", Structure, May 2008; 16(5): 705-714.
Jung et al., "Toll-Like Receptor 4 Decoy, TOY, Attenuates Gram-Negative Bacterial Sepsis," PLoS One, vol. 4, No. 10, e7403 (Oct. 9, 2009).

(Continued)

*Primary Examiner* — Brian J Gangle
*Assistant Examiner* — Andrea McCollum
(74) *Attorney, Agent, or Firm* — Joseph R. Baker, Jr.; Gavrilovich, Dodd & Lindsey LLP

(57) ABSTRACT

The present invention relates to a soluble polypeptide comprised of repeat modules. More particularly, the present invention relates to a soluble fusion polypeptide of the N-terminal domain of internalin and LRR (Leucine rich repeat) family protein, a method for preparing the polypeptide, a vector comprising a nucleic acid sequence encoding the polypeptide, a host cell comprising the vector, a method for producing a solubility and folding-improved fusion polypeptide by expressing the vector in the host cell, and a method for improving the solubility and folding of the fusion polypeptide. Further, the present invention relates to a method for preparing the polypeptide bound with a specific target and analyzing the efficacy of the soluble polypeptide.

2 Claims, 31 Drawing Sheets

(56) References Cited

OTHER PUBLICATIONS

Lee S.-C. et al. "Design of a binding scaffold based on variable lymphocyte receptors of jawless vertebrates by module engineering," Proceedings of the National Academy of Sciences USA (2012) 109(9): 3299-3304.

Mitsuzawa et al., "Recombinant Soluble Forms of Extracellular TLR4 Domain and MD-2 Inhibit Lipopolysachharide Binding on Cell Surface and Dampen Lipopolysaccharide-Induced Pulmonary Inflammation in Mice", J. Immunol. 2006; 177:8133-8139.

Triantafilou et al., "Sepsis: molecular mechanisms underlying lipopolysaccharide recognition", Expert Reviews in Molecular Medicine, vol. 6, Feb. 13, 2004, pp. 1-18.

Wezner-Ptasinska M. et al. "Design and characteristics of a stable protein scaffold for specific binding based on variable lymphocyte receptor sequences," Biochimica et Biophysica Acta (2011) 1814(9): 1140-1145.

* cited by examiner

MMFALRGTCVLLALLLGCRNG

KACPSRCSCSGTIVECYSQGRTSVPTGIPAQTTYLDLETNSLKSLPNGVFDE

LTSLTQLYLGGNKLQSLPNGVFNK

LTSLTYLNLSTNQLQSLPNGVFDK

LTQLKELALNTNQLQSLPDGVFDK

LTQLKDLRLYQNQLKSVPDGVFDR

LTSLQYIWLHDNPWDCTCPGIRYLSEWINKHSGVVRNSAGSVAPDSAKCSGSGKPVRSIICPT

TTTTTTTTMPTTTLPTTTKMSMVKVPLVPPEAFGRVMNACAVFPSYIFLHLVHGLAAVPLVYLICHASQLL

FIGURE 1

KACPSRCSCSGTVECYSQGRTSVPTGIPAQTTYLDLETNSLKSLPNGVFDE

LTSLTQLDLSRNKLQSLPNGVFNK

LTSLTYLJLTGNQLQSLPNGVFDK

LTQLKELVLVENQLQSLPDGVFDK

LTKLTYLNLAHNELQSLPKGVFDK

LTSLKELDLSYNQLKRVPEGAFDK

LTQLKDLRLYQNQLKSVPDGVFDR

LTSLQYIWLHDNPWDCTCPGIRYLSEWINKHSGVVRNSAGGSVAPDSAKCSGSGKPVRSIICPT

FIGURE 2

TTDPKACPSRCSCSGTTVECYSQGRTSVPTGIPAQTTYLDLETNSLKSLPNGVFDE

LTNLTQLDLSRNQLQSLPNGVFDK
LTNLTYLILTGNQLQSLPNGVFDK
LTNLKELVLVENQLQSLPDGVFDK
LTNLTYLNLAHNQLQSLPKGVFDK
LTNLTELDLSYNQLQSLPEGVFDK

LTQLKDLRLYQNQLKSVPDGVFDR

LTSLQYIWLHDNPWDCTCPGIRYLSEWINKHSGVVRNSAGSVAPDSAKCSGSGKPVRSIICPTLEV

FIGURE 3

ETTVSTPIKQFPDDAFAETIKANLKKKSVTDAVTQNE

LNSIDQLIANNSDIKSVQGIQY

LPNVTKLFLNGNKLTDIKPLTN

LTNLTYLILTGNQLQSLPNGVFDK

LTNLKELVLVENQLQSLPDGVFDK

LTNLTYLNLAHNQLSLPKGVFDK

LTNLTELDLSYNQLQSLPEGVFDK

LTQLKDLRLYQNQLKSVPDGVFDR

LTSLQYIWLHDNPWDCTCPGIRYLSEWINKHSGVVRNSAGSVAPDSAKCSGSGKPVRSIICPTLEV

FIGURE 5

ETTVSTPIKQJFPDDAFAETIKANLKKKSVTDAVTQNE

LNSIDQIIANNSDIKSVQGIQY

LPNVLVLRLGGNNLRDISALEK

LTSLTYLILTGNQLQSLPNGVFDK

LTQLKELVLVENQLQSLPDGVFDK

LTKLTYLNLAHNELQSLPKGVFDK

LTSLKELDLSYNQLKRVPEGAFDK

LTQLKDLRLYQNQLKSVPDGVFDR

LTSLQYIWLHDNPWDCTCPGIRVLSEWINKHSGVVRNSAGSVAPDSAKCSGSGKPVRSIICPTLEV

FIGURE 6

ETTTVSTPFKQFFPDQAFAETIKANLKKKSVTDAVTQNE
LNSIDQTIANNSDIKSVQGIQY
LPNVRYLALGGNKLLHDISALKE

LTNLTYLILTGNQLQSLPNGVFDK
LTNLKELVLVENQLQSLPDGVFDK
LTNLTYLNLAHNQLQSLPKGVFDK
LTNLTELDLSYNQLQSLPEGVFDK
LTQLKDLRLYQNQLKSVPDGVFDR
LTSLQYIWLHDNPWDCTCPGIRYLSEWINKHSGVVRNSAGSVAPDSAKCSGSGKPVRSIICPTLEV

FIGURE 7

ETTTVSTPIKQJFPDDAFAETIKANLKKKSVTDAVTQNE

LNSIDQTIANNSDIKSVQGIQY

LPNVKYLRLGGMNLRDISALEK

LTNLTVLDLSRNQLSLPNGVFDK

LTSLTYLILTGNQLQSLPNGVFDK

LTQLKELVLVENQLQSLPDGVFDK

LTKLTYLNLAHNELQSLPKGVFDK

LTSLKELDLSYNQLKRVPEGAFDK

LTQLKDLRLYQNQLKSVPDGVFDR

LTSLQYIWLHDNPWDCTCPGIRYLSEWINKHSGVVRNSAGSVAPDSAKCSGSGKPVRSIICPT

FIGURE 10

ETITVSTPIKQIFPDDAFAETIKANLKKKSVTDAVTQNE

LNSIDQIIANNSDIKSVQGIQY

LPNVRYLALGGNKLHDISALKE

LTNLTVLDLSRNQLQSLPNGVFDK

LTNLTYLILTGNQLQSLPNGVFDK

LTNLKELVLVENQLQSLPDGVFDK

LTNLTYLNLAHNQLQSLPKGVFDK

LTNLTELDLSYNQLQSLPEGVFDKL

TQLKDLRLYQNQLKSVPDGVFDR

LTSLQYIWLHDNPWDCTCPGIRYLSEWINKHSGVVRNSAGSVAPDSAKCSGSGKPVRSIICPT

ETTVSTPIKQEFPDDAFAETIKANLKKKSVTDAVTQNE

LNSIDQIIANNSDIKSVQGIQY

LPNVRYLALGGNKLHDISALKE

LNLTYLQLTGNQLQSLPNGVFDK

LPELQVLDLSRNEIQTIEDGAFQS

LSHLSTLILTGNPIQSLALGAFSG

LSSLQKLVAVETNLASLENFPIGH

LKTLKELNVAHNLIQSFKLPEYFSNLITNLEHDLSSNKIQSIYCTDLRVLHQMPLLNLSLDLSLNPMNFIQPGAFKE

RLKELALDTNQLKSVPDGIFDRLTSLQKIWLHTNPWDCSCPRIDYLSRWLNKNSQKEQGSAKCSGSGKPVRSIICP

ETITVSTPIKQIFPDDAFAETIKANLAKMLSVTDAVTQME

LMSIDQIIAMNSDIKSVQGIQY

LPNVKYLRLGGNRLRDISALEK

LTSLTYLNLSTNQLQSLPNGVFDK

LTQLKELALNTNQLQSLPDGVFDK

LTKLTYLSLGYNELQSLPKGVFDK

LTSLKELRLYNNQLKRVPEGAFDK

LTQLKDLRLYQNQLKSVPDGVFDR

LTSLQYIWLHDNPWDCTCPGIRYLSEWINKHSGVVRNSAGSVAPDSAKCSGSGKPVRSIIQPT

FIGURE 20

ETIITVSTPIKQIFPDDAFAETIKANLKKKSVTDAVTQNE

LNSIDQIIANNSDIKSVQGIQY

LPNVKYLRLGGNNLRDISALEK

LTSLTYLILTGNQLQSLPNGVFDK

LTQLKELVLVENQLQSLPDGVFDK

LTKLTYLNLAHNELQSLPKGVFDK

LTSLKELDLSYNQLKRVPEGAFDK

LTQLKDLRLYQNQLKSVPDGVFDR

LTSLQYIWLHDNPWDCTCPGIRYLSEWINKHSGVVRNSAGSVAPDSAKCSGSGKPVRSIICPT

FIGURE 21

ETIIVSTPIKQIFPDDAFAETIKANLKKKSVTDAVTQME

LNSIDDIAMNSDIKSVQQIQY

LPNVRYLJLQQMKLHDISALKE

LTNLTYLILTGNQLQSLPNGVFDK

LTNLKELVLVENQLQSLPDGVFDK

LTNLTYLNLAHNQLQSLPKGVFDK

LTNLTELDLSYNQLQSLPEGVFDK

LTQLKDLRLYQNQLKSVPDGVFDR

LTSLQYIWLHDNPWDCTCPGIRYLSEWINKHSGVVRNSAGSVAPDSAKCSGSGKPVRSIIQPT

FIGURE 22

ETITVSTPIKQIFPDDAFAETIKANLKKKSVTDAVTQME

LNSIDTIQAMESDIKSVQGIQY

LPWKQLDLSPNMLRDISALEK

LTNLTYLDLSRNQLQSLPNGVFDK

LTSLTYLILTGNQLQSLPNGVFDK

LTQLKELVLVENQLQSLPDGVFDK

LTKLTYLNLAHNELQSLPKGVFDK

LTSLKELDLSYNQLKRVPEGAFDK

LTQLKDLRLYQNQLKSVPDGVFDR

LTSLQYIWLHDNPWDCTCPGIRYLSEWINKHSGVVRNSAGSVAPDSAKCSGSGKPVRSIICPT

FIGURE 23

ETITYSTPIKOIFPDDAFAETIKAHLKKKSVTDAVTDHE

LNSIDTIQAMESDIKSVQDIQY

LPNVDELDLSPHKLLADIQALKE

LTNLTVLDLSRNQLQSLPNGVFDK

LTNLTYLILTGNQLQSLPNGVFDK

LTNLKELVLVENQLQSLPDGVFDK

LTNLTYLNLAHNQLQSLPKGVFDK

LTNLTELDLSYNQLQSLPEGVFDK

LTQLKDLRLYQNQLKSVPDGVFDR

LTSLQYIWLHDNPWDCTCPGIRYLSEWINKHSGVVRNSAGSVAPDSAKCSGSGKPVRSIICPT

FIGURE 24

ETTVSTPIKQIFPDDAPAETIKAMLKKKGSVTDAVTQME

LMSIDQIIAMNSDIKSVQGIQY

LPNVRYLALGGMKLHDISALKE

LTNLxxLxLxxNQLQSLPxGVFDK

LTNLxxLxLxxNQLQSLPxGVFDK

LTNLxxLxLxxNQLQSLPxGVFDK

LTNLxxLxLxxNQLQSLPxGVFDK

LTQLKDLRLYQNQLKSVPDGVFDR

LTSLQYIWLHDNPWDCTCPGIRYLSEWINKHSGVVRNSAGSVAPDSAKCSGSGKPVRSIICPT

FIGURE 25

SEQUENCE LISTING

<160> NUMBER OF SEQ ID NOS: 24

<210> SEQ ID NO 1
<211> LENGTH: 305
<212> TYPE: PRT

<213> ORGANISM: Artificial Sequence
<220> FEATURE:
<223> OTHER INFORMATION: EB8VLRB.59

<400> SEQUENCE: 1

Met Lys Phe Ala Leu Arg Gly Thr Cys Val Leu Leu Ala Leu Leu Leu
1               5                   10                  15

Cys Cys Arg Asn Gly Lys Ala Cys Pro Ser Arg Cys Ser Cys Ser Gly
                20                  25                  30

Thr Thr Val Glu Cys Tyr Ser Gln Gly Arg Thr Ser Val Pro Thr Gly
            35                  40                  45

Ile Pro Ala Gln Thr Thr Tyr Leu Asp Leu Glu Thr Asn Ser Leu Lys
    50                  55                  60

Ser Leu Pro Asn Gly Val Phe Asp Glu Leu Thr Ser Leu Thr Gln Leu
65                  70                  75                  80

Tyr Leu Gly Gly Asn Lys Leu Gln Ser Leu Pro Asn Gly Val Phe Asn
                85                  90                  95

Lys Leu Thr Ser Leu Thr Tyr Leu Asn Leu Ser Thr Asn Gln Leu Gln
                100                 105                 110

Ser Leu Pro Asn Gly Val Phe Asp Lys Leu Thr Gln Leu Lys Glu Leu
            115                 120                 125

Ala Leu Asn Thr Asn Gln Leu Gln Ser Leu Pro Asp Gly Val Phe Asp
    130                 135                 140

Lys Leu Thr Gln Leu Lys Asp Leu Arg Leu Tyr Gln Asn Gln Leu Lys
145                 150                 155                 160

Ser Val Pro Asp Gly Val Phe Asp Arg Leu Thr Ser Leu Gln Tyr Ile
                165                 170                 175

Trp Leu His Asp Asn Pro Trp Asp Cys Thr Cys Pro Gly Ile Arg Tyr
                180                 185                 190

Leu Ser Glu Trp Ile Asn Lys His Ser Gly Val Val Arg Asn Ser Ala
            195                 200                 205

Gly Ser Val Ala Pro Asp Ser Ala Lys Cys Ser Gly Ser Gly Lys Pro
    210                 215                 220

Val Arg Ser Ile Ile Cys Pro Thr Thr Thr Thr Thr Thr Thr Thr Thr
225                 230                 235                 240

Thr Met Pro Thr Thr Thr Thr Leu Pro Thr Thr Thr Lys Met Ser Met
                245                 250                 255

Val Lys Val Pro Leu Val Pro Pro Glu Ala Phe Gly Arg Val Met Asn
                260                 265                 270

Ala Cys Ala Tyr Phe Pro Ser Tyr Ile Phe Leu His Leu Val His Gly
            275                 280                 285

Leu Ala Ala Val Pro Leu Val Tyr Leu Ile Cys His Ala Ser Gln Leu
    290                 295                 300

Leu
305

<210> SEQ ID NO 2
<211> LENGTH: 259
<212> TYPE: PRT
<213> ORGANISM: Artificial Sequence
<220> FEATURE:
<223> OTHER INFORMATION: VLR5n

<400> SEQUENCE: 2

Lys Ala Cys Pro Ser Arg Cys Ser Cys Ser Gly Thr Thr Val Glu Cys
1               5                   10                  15

Tyr Ser Gln Gly Arg Thr Ser Val Pro Thr Gly Ile Pro Ala Gln Thr
            20                  25                  30

Thr Tyr Leu Asp Leu Glu Thr Asn Ser Leu Lys Ser Leu Pro Asn Gly
        35                  40                  45

Val Phe Asp Glu Leu Thr Ser Leu Thr Gln Leu Asp Leu Ser Arg Asn
50                  55                  60

Lys Leu Gln Ser Leu Pro Asn Gly Val Phe Asn Lys Leu Thr Ser Leu
65                  70                  75                  80

Thr Tyr Leu Ile Leu Thr Gly Asn Gln Leu Gln Ser Leu Pro Asn Gly
            85                  90                  95

Val Phe Asp Lys Leu Thr Gln Leu Lys Glu Leu Val Leu Val Glu Asn
                100                 105                 110

Gln Leu Gln Ser Leu Pro Asp Gly Val Phe Asp Lys Leu Thr Lys Leu
            115                 120                 125

Thr Tyr Leu Asn Leu Ala His Asn Glu Leu Gln Ser Leu Pro Lys Gly
        130                 135                 140

Val Phe Asp Lys Leu Thr Ser Leu Lys Glu Leu Asp Leu Ser Tyr Asn
145                 150                 155                 160

Gln Leu Lys Arg Val Pro Glu Gly Ala Phe Asp Lys Leu Thr Gln Leu
            165                 170                 175

Lys Asp Leu Arg Leu Tyr Gln Asn Gln Leu Lys Ser Val Pro Asp Gly
                180                 185                 190

Val Phe Asp Arg Leu Thr Ser Leu Gln Tyr Ile Trp Leu His Asp Asn
            195                 200                 205

Pro Trp Asp Cys Thr Cys Pro Gly Ile Arg Tyr Leu Ser Glu Trp Ile
    210                 215                 220

Asn Lys His Ser Gly Val Val Arg Asn Ser Ala Gly Ser Val Ala Pro
225                 230                 235                 240

Asp Ser Ala Lys Cys Ser Gly Ser Gly Lys Pro Val Arg Ser Ile Ile
                245                 250                 255

Cys Pro Thr

<210> SEQ ID NO 3
<211> LENGTH: 266
<212> TYPE: PRT
<213> ORGANISM: Artificial Sequence
<220> FEATURE:
<223> OTHER INFORMATION: VLR5c

<400> SEQUENCE: 3

Thr Thr Asp Pro Lys Ala Cys Pro Ser Arg Cys Ser Cys Ser Gly Thr
1               5                   10                  15

Thr Val Glu Cys Tyr Ser Gln Gly Arg Thr Ser Val Pro Thr Gly Ile
            20                  25                  30

Pro Ala Gln Thr Thr Tyr Leu Asp Leu Glu Thr Asn Ser Leu Lys Ser
        35                  40                  45

Leu Pro Asn Gly Val Phe Asp Glu Leu Thr Asn Leu Thr Gln Leu Asp
50                  55                  60

Leu Ser Arg Asn Gln Leu Gln Ser Leu Pro Asn Gly Val Phe Asp Lys
65                  70                  75                  80

Leu Thr Asn Leu Thr Tyr Leu Ile Leu Thr Gly Asn Gln Leu Gln Ser
            85                  90                  95

Leu Pro Asn Gly Val Phe Asp Lys Leu Thr Asn Leu Lys Glu Leu Val
                100                 105                 110

Leu Val Glu Asn Gln Leu Gln Ser Leu Pro Asp Gly Val Phe Asp Lys

```
                115                 120                 125
Leu Thr Asn Leu Thr Tyr Leu Asn Leu Ala His Asn Gln Leu Gln Ser
        130                 135                 140

Leu Pro Lys Gly Val Phe Asp Lys Leu Thr Asn Leu Thr Glu Leu Asp
145                 150                 155                 160

Leu Ser Tyr Asn Gln Leu Gln Ser Leu Pro Glu Gly Val Phe Asp Lys
                165                 170                 175

Leu Thr Gln Leu Lys Asp Leu Arg Leu Tyr Gln Asn Gln Leu Lys Ser
            180                 185                 190

Val Pro Asp Gly Val Phe Asp Arg Leu Thr Ser Leu Gln Tyr Ile Trp
            195                 200                 205

Leu His Asp Asn Pro Trp Asp Cys Thr Cys Pro Gly Ile Arg Tyr Leu
        210                 215                 220

Ser Glu Trp Ile Asn Lys His Ser Gly Val Val Arg Asn Ser Ala Gly
225                 230                 235                 240

Ser Val Ala Pro Asp Ser Ala Lys Cys Ser Gly Ser Gly Lys Pro Val
                245                 250                 255

Arg Ser Ile Ile Cys Pro Thr Leu Glu Val
            260                 265

<210> SEQ ID NO 4
<211> LENGTH: 207
<212> TYPE: PRT
<213> ORGANISM: Artificial Sequence
<220> FEATURE:
<223> OTHER INFORMATION: Internalin B (InlB) derived from Listeria
      monocytogenes

<400> SEQUENCE: 4

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Thr Lys Leu Phe Leu Asn Gly Asn Lys Leu Thr Asp Ile Lys Pro
65                  70                  75                  80

Leu Thr Asn Leu Lys Asn Leu Gly Trp Leu Phe Leu Asp Glu Asn Lys
                85                  90                  95

Ile Lys Asp Leu Ser Ser Leu Lys Asp Leu Lys Lys Leu Lys Ser Leu
            100                 105                 110

Ser Leu Glu His Asn Gly Ile Ser Asp Ile Asn Gly Leu Val His Leu
        115                 120                 125

Pro Gln Leu Glu Ser Leu Tyr Leu Gly Asn Asn Lys Ile Thr Asp Ile
    130                 135                 140

Thr Val Leu Ser Arg Leu Thr Lys Leu Asp Thr Leu Ser Leu Glu Asp
145                 150                 155                 160

Asn Gln Ile Ser Asp Ile Val Pro Leu Ala Gly Leu Thr Lys Leu Gln
                165                 170                 175

Asn Leu Tyr Leu Ser Lys Asn His Ile Ser Asp Leu Arg Ala Leu Ala
            180                 185                 190

Gly Leu Lys Asn Leu Asp Val Leu Glu Leu Phe Ser Gln Glu Cys
        195                 200                 205
```

```
<210> SEQ ID NO 5
<211> LENGTH: 269
<212> TYPE: PRT
<213> ORGANISM: Artificial Sequence
<220> FEATURE:
<223> OTHER INFORMATION: Fused polypeptide for InlB-VLR5n

<400> SEQUENCE: 5

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Thr Lys Leu Phe Leu Asn Gly Asn Lys Leu Thr Asp Ile Lys Pro
65                  70                  75                  80

Leu Thr Asn Leu Thr Ser Leu Thr Tyr Leu Ile Leu Thr Gly Asn Gln
                85                  90                  95

Leu Gln Ser Leu Pro Asn Gly Val Phe Asp Lys Leu Thr Gln Leu Lys
            100                 105                 110

Glu Leu Val Leu Val Glu Asn Gln Leu Gln Ser Leu Pro Asp Gly Val
        115                 120                 125

Phe Asp Lys Leu Thr Lys Leu Thr Tyr Leu Asn Leu Ala His Asn Glu
    130                 135                 140

Leu Gln Ser Leu Pro Lys Gly Val Phe Asp Lys Leu Thr Ser Leu Lys
145                 150                 155                 160

Glu Leu Asp Leu Ser Tyr Asn Gln Leu Lys Arg Val Pro Glu Gly Ala
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
            260                 265

<210> SEQ ID NO 6
<211> LENGTH: 269
<212> TYPE: PRT
<213> ORGANISM: Artificial Sequence
<220> FEATURE:
<223> OTHER INFORMATION: Fused polypeptide for InlB-VLR5c

<400> SEQUENCE: 6

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45
```

```
Asn Asn Ser Asp Ile Lys Ser Val Gln Gly Ile Gln Tyr Leu Pro Asn
            50                  55                  60

Val Thr Lys Leu Phe Leu Asn Gly Asn Lys Leu Thr Asp Ile Lys Pro
65                  70                  75                  80

Leu Thr Asn Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
            115                 120                 125

Phe Asp Lys Leu Thr Asn Leu Thr Tyr Leu Asn Leu Ala His Asn Gln
            130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr Leu Glu Val
            260                 265

<210> SEQ ID NO 7
<211> LENGTH: 269
<212> TYPE: PRT
<213> ORGANISM: Artificial Sequence
<220> FEATURE:
<223> OTHER INFORMATION: Fused polypeptide for InlB-VLR5n-Rosetta

<400> SEQUENCE: 7

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
            50                  55                  60

Val Lys Tyr Leu Arg Leu Gly Gly Asn Asn Leu Arg Asp Ile Ser Ala
65                  70                  75                  80

Leu Glu Lys Leu Thr Ser Leu Thr Tyr Leu Ile Leu Thr Gly Asn Gln
                85                  90                  95

Leu Gln Ser Leu Pro Asn Gly Val Phe Asp Lys Leu Thr Gln Leu Lys
            100                 105                 110

Glu Leu Val Leu Val Glu Asn Gln Leu Gln Ser Leu Pro Asp Gly Val
            115                 120                 125

Phe Asp Lys Leu Thr Lys Leu Thr Tyr Leu Asn Leu Ala His Asn Glu
            130                 135                 140
```

Leu Gln Ser Leu Pro Lys Gly Val Phe Asp Lys Leu Thr Ser Leu Lys
145                 150                 155                 160

Glu Leu Asp Leu Ser Tyr Asn Gln Leu Lys Arg Val Pro Glu Gly Ala
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
            260                 265

<210> SEQ ID NO 8
<211> LENGTH: 269
<212> TYPE: PRT
<213> ORGANISM: Artificial Sequence
<220> FEATURE:
<223> OTHER INFORMATION: Fused polypeptide for InlB-VLR5c-Rosetta

<400> SEQUENCE: 8

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
                20                  25                  30

Asp Ala Val Thr Gln Asn Glu Leu Asn Ser Ile Asp Gln Ile Ile Ala
            35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Tyr Leu Ile Leu Thr Gly Asn Gln
                85                  90                  95

Leu Gln Ser Leu Pro Asn Gly Val Phe Asp Lys Leu Thr Asn Leu Lys
            100                 105                 110

Glu Leu Val Leu Val Glu Asn Gln Leu Gln Ser Leu Pro Asp Gly Val
        115                 120                 125

Phe Asp Lys Leu Thr Asn Leu Thr Tyr Leu Asn Leu Ala His Asn Gln
        130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
                195                 200                 205

Tyr Ile Trp Leu His Asp Asn Pro Trp Asp Cys Thr Cys Pro Gly Ile
            210                 215                 220

Arg Tyr Leu Ser Glu Trp Ile Asn Lys His Ser Gly Val Val Arg Asn
225                 230                 235                 240

```
Ser Ala Gly Ser Val Ala Pro Asp Ser Ala Lys Cys Ser Gly Ser Gly
                245                 250                 255

Lys Pro Val Arg Ser Ile Ile Cys Pro Thr Leu Glu Val
            260                 265
```

<210> SEQ ID NO 9
<211> LENGTH: 290
<212> TYPE: PRT
<213> ORGANISM: Artificial Sequence
<220> FEATURE:
<223> OTHER INFORMATION: Fused polypedide for InlB-VLR6n

<400> SEQUENCE: 9

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Lys Tyr Leu Arg Leu Gly Gly Asn Asn Leu Arg Asp Ile Ser Ala
65                  70                  75                  80

Leu Glu Lys Leu Thr Asn Leu Thr Val Leu Asp Leu Ser Arg Asn Gln
                85                  90                  95

Leu Gln Ser Leu Pro Asn Gly Val Phe Asp Lys Leu Thr Ser Leu Thr
            100                 105                 110

Tyr Leu Ile Leu Thr Gly Asn Gln Leu Gln Ser Leu Pro Asn Gly Val
        115                 120                 125

Phe Asp Lys Leu Thr Gln Leu Lys Glu Leu Val Leu Val Glu Asn Gln
    130                 135                 140

Leu Gln Ser Leu Pro Asp Gly Val Phe Asp Lys Leu Thr Lys Leu Thr
145                 150                 155                 160

Tyr Leu Asn Leu Ala His Asn Glu Leu Gln Ser Leu Pro Lys Gly Val
                165                 170                 175

Phe Asp Lys Leu Thr Ser Leu Lys Glu Leu Asp Leu Ser Tyr Asn Gln
            180                 185                 190

Leu Lys Arg Val Pro Glu Gly Ala Phe Asp Lys Leu Thr Gln Leu Lys
        195                 200                 205

Asp Leu Arg Leu Tyr Gln Asn Gln Leu Lys Ser Val Pro Asp Gly Val
    210                 215                 220

Phe Asp Arg Leu Thr Ser Leu Gln Tyr Ile Trp Leu His Asp Asn Pro
225                 230                 235                 240

Trp Asp Cys Thr Cys Pro Gly Ile Arg Tyr Leu Ser Glu Trp Ile Asn
                245                 250                 255

Lys His Ser Gly Val Val Arg Asn Ser Ala Gly Ser Val Ala Pro Asp
            260                 265                 270

Ser Ala Lys Cys Ser Gly Ser Gly Lys Pro Val Arg Ser Ile Ile Cys
        275                 280                 285

Pro Thr
    290
```

<210> SEQ ID NO 10
<211> LENGTH: 290
<212> TYPE: PRT
<213> ORGANISM: Artificial Sequence
<220> FEATURE:
<223> OTHER INFORMATION: Fused polypeptide for InlB-VLR6c

<400> SEQUENCE: 10

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Thr Val Leu Asp Leu Ser Arg Asn Gln
            85                  90                  95

Leu Gln Ser Leu Pro Asn Gly Val Phe Asp Lys Leu Thr Asn Leu Thr
        100                 105                 110

Tyr Leu Ile Leu Thr Gly Asn Gln Leu Gln Ser Leu Pro Asn Gly Val
    115                 120                 125

Phe Asp Lys Leu Thr Asn Leu Lys Glu Leu Val Leu Val Glu Asn Gln
130                 135                 140

Leu Gln Ser Leu Pro Asp Gly Val Phe Asp Lys Leu Thr Asn Leu Thr
145                 150                 155                 160

Tyr Leu Asn Leu Ala His Asn Gln Leu Gln Ser Leu Pro Lys Gly Val
            165                 170                 175

Phe Asp Lys Leu Thr Asn Leu Thr Glu Leu Asp Leu Ser Tyr Asn Gln
        180                 185                 190

Leu Gln Ser Leu Pro Glu Gly Val Phe Asp Lys Leu Thr Gln Leu Lys
    195                 200                 205

Asp Leu Arg Leu Tyr Gln Asn Gln Leu Lys Ser Val Pro Asp Gly Val
210                 215                 220

Phe Asp Arg Leu Thr Ser Leu Gln Tyr Ile Trp Leu His Asp Asn Pro
225                 230                 235                 240

Trp Asp Cys Thr Cys Pro Gly Ile Arg Tyr Leu Ser Glu Trp Ile Asn
            245                 250                 255

Lys His Ser Gly Val Val Arg Asn Ser Ala Gly Ser Val Ala Pro Asp
        260                 265                 270

Ser Ala Lys Cys Ser Gly Ser Gly Lys Pro Val Arg Ser Ile Ile Cys
    275                 280                 285

Pro Thr
    290

<210> SEQ ID NO 11
<211> LENGTH: 276
<212> TYPE: PRT
<213> ORGANISM: Artificial Sequence
<220> FEATURE:
<223> OTHER INFORMATION: TV3

<400> SEQUENCE: 11

Glu Pro Cys Val Glu Val Val Pro Asn Ile Thr Tyr Gln Cys Met Glu
1               5                   10                  15

Leu Asn Phe Tyr Lys Ile Pro Asp Asn Leu Pro Phe Ser Thr Lys Asn
            20                  25                  30

Leu Asp Leu Ser Phe Asn Pro Leu Arg His Leu Gly Ser Tyr Ser Phe

```
                35                  40                  45
Phe Ser Phe Pro Glu Leu Gln Val Leu Asp Leu Ser Arg Cys Glu Ile
 50                  55                  60

Gln Thr Ile Glu Asp Gly Ala Tyr Gln Ser Leu Ser His Leu Ser Thr
 65                  70                  75                  80

Leu Ile Leu Thr Gly Asn Pro Ile Gln Ser Leu Ala Leu Gly Ala Phe
                 85                  90                  95

Ser Gly Leu Ser Ser Leu Gln Lys Leu Val Ala Val Glu Thr Asn Leu
            100                 105                 110

Ala Ser Leu Glu Asn Phe Pro Ile Gly His Leu Lys Thr Leu Lys Glu
        115                 120                 125

Leu Asn Val Ala His Asn Leu Ile Gln Ser Phe Lys Leu Pro Glu Tyr
    130                 135                 140

Phe Ser Asn Leu Thr Asn Leu Glu His Leu Asp Leu Ser Ser Asn Lys
145                 150                 155                 160

Ile Gln Ser Ile Tyr Cys Thr Asp Leu Arg Val Leu His Gln Met Pro
                165                 170                 175

Leu Leu Asn Leu Ser Leu Asp Leu Ser Leu Asn Pro Met Asn Phe Ile
            180                 185                 190

Gln Pro Gly Ala Phe Lys Glu Ile Arg Leu Lys Glu Leu Ala Leu Asp
        195                 200                 205

Thr Asn Gln Leu Lys Ser Val Pro Asp Gly Ile Phe Asp Arg Leu Thr
    210                 215                 220

Ser Leu Gln Lys Ile Trp Leu His Thr Asn Pro Trp Asp Cys Ser Cys
225                 230                 235                 240

Pro Arg Ile Asp Tyr Leu Ser Arg Trp Leu Asn Lys Asn Ser Gln Lys
                245                 250                 255

Glu Gln Gly Ser Ala Lys Cys Ser Gly Ser Gly Lys Pro Val Arg Ser
            260                 265                 270

Ile Ile Cys Pro
        275

<210> SEQ ID NO 12
<211> LENGTH: 333
<212> TYPE: PRT
<213> ORGANISM: Artificial Sequence
<220> FEATURE:
<223> OTHER INFORMATION: Fused polypeptide for InlB-VLR-TV3

<400> SEQUENCE: 12

Glu Thr Ile Thr Val Ser Thr Pro Ile Lys Gln Ile Phe Pro Asp Asp
 1               5                  10                  15

Ala Phe Ala Glu Thr Ile Lys

```
                       115                 120                 125
Phe Gln Ser Leu Ser His Leu Ser Thr Leu Ile Leu Thr Gly Asn Pro
130                 135                 140

Ile Gln Ser Leu Ala Leu Gly Ala Phe Ser Gly Leu Ser Ser Leu Gln
145                 150                 155                 160

Lys Leu Val Ala Val Glu Thr Asn Leu Ala Ser Leu Glu Asn Phe Pro
                    165                 170                 175

Ile Gly His Leu Lys Thr Leu Lys Glu Leu Asn Val Ala His Asn Leu
                180                 185                 190

Ile Gln Ser Phe Lys Leu Pro Glu Tyr Phe Ser Asn Leu Thr Asn Leu
            195                 200                 205

Glu His Leu Asp Leu Ser Ser Asn Lys Ile Gln Ser Ile Tyr Cys Thr
        210                 215                 220

Asp Leu Arg Val Leu His Gln Met Pro Leu Leu Asn Leu Ser Leu Asp
225                 230                 235                 240

Leu Ser Leu Asn Pro Met Asn Phe Ile Gln Pro Gly Ala Phe Lys Glu
                    245                 250                 255

Ile Arg Leu Lys Glu Leu Ala Leu Asp Thr Asn Gln Leu Lys Ser Val
                    260                 265                 270

Pro Asp Gly Ile Phe Asp Arg Leu Thr Ser Leu Gln Lys Ile Trp Leu
                275                 280                 285

His Thr Asn Pro Trp Asp Cys Ser Cys Pro Arg Ile Asp Tyr Leu Ser
290                 295                 300

Arg Trp Leu Asn Lys Asn Ser Gln Lys Glu Gln Gly Ser Ala Lys Cys
305                 310                 315                 320

Ser Gly Ser Gly Lys Pro Val Arg Ser Ile Ile Cys Pro
                    325                 330

<210> SEQ ID NO 13
<211> LENGTH: 83
<212> TYPE: PRT
<213> ORGANISM: Artificial Sequence
<220> FEATURE:
<223> OTHER INFORMATION: N-terminal of Internalin B
<220> FEATURE:
<221> NAME/KEY: MISC_FEATURE
<222> LOCATION: (64)..(64)
<223> OTHER INFORMATION: Xaa is a hydrophilic amino acid
<220> FEATURE:
<221> NAME/KEY: MISC_FEATURE
<222> LOCATION: (66)..(67)
<223> OTHER INFORMATION: Xaa is a hydrophilic amino acid
<220> FEATURE:
<221> NAME/KEY: MISC_FEATURE
<222> LOCATION: (69)..(69)
<223> OTHER INFORMATION: Xaa is a hydrophilic amino acid
<220> FEATURE:
<221> NAME/KEY: MISC_FEATURE
<222> LOCATION: (71)..(72)
<223> OTHER INFORMATION: Xaa is a hydrophilic amino acid
<220> FEATURE:
<221> NAME/KEY: MISC_FEATURE
<222> LOCATION: (74)..(74)
<223> OTHER INFORMATION: Xaa is a hydrophilic amino acid
<220> FEATURE:
<221> NAME/KEY: MISC_FEATURE
<222> LOCATION: (76)..(76)
<223> OTHER INFORMATION: Xaa is a hydrophilic amino acid
<220> FEATURE:
<221> NAME/KEY: MISC_FEATURE
<222> LOCATION: (79)..(80)
<223> OTHER INFORMATION: Xaa is a hydrophilic amino acid
<220> FEATURE:
<221> NAME/KEY: MISC_FEATURE
<222> LOCATION: (82)..(83)
```

<223> OTHER INFORMATION: Xaa is a hydrophilic amino acid

<400> SEQUENCE: 13

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Xaa
    50                  55                  60

Leu Xaa Xaa Leu Xaa Leu Xaa Xaa Asn Xaa Ile Xaa Asp Ile Xaa Xaa
65                  70                  75                  80

Leu Xaa Xaa
```

<210> SEQ ID NO 14
<211> LENGTH: 266
<212> TYPE: PRT
<213> ORGANISM: Artificial Sequence
<220> FEATURE:
<223> OTHER INFORMATION: IVLRn

<400> SEQUENCE: 14

```
Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Lys Tyr Leu Arg Leu Gly Gly Asn Asn Leu Arg Asp Ile Ser Ala
65                  70                  75                  80

Leu Glu Lys Leu Thr Ser Leu Thr Tyr Leu Asn Leu Ser Thr Asn Gln
                85                  90                  95

Leu Gln Ser Leu Pro Asn Gly Val Phe Asp Lys Leu Thr Gln Leu Lys
            100                 105                 110

Glu Leu Ala Leu Asn Thr Asn Gln Leu Gln Ser Leu Pro Asp Gly Val
        115                 120                 125

Phe Asp Lys Leu Thr Lys Leu Thr Tyr Leu Ser Leu Gly Tyr Asn Glu
    130                 135                 140

Leu Gln Ser Leu Pro Lys Gly Val Phe Asp Lys Leu Thr Ser Leu Lys
145                 150                 155                 160

Glu Leu Arg Leu Tyr Asn Asn Gln Leu Lys Arg Val Pro Glu Gly Ala
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255
```

```
Lys Pro Val Arg Ser Ile Ile Cys Pro Thr
            260                 265

<210> SEQ ID NO 15
<211> LENGTH: 266
<212> TYPE: PRT
<213> ORGANISM: Artificial Sequence
<220> FEATURE:
<223> OTHER INFORMATION: IVLRn-MD-2

<400> SEQUENCE: 15

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
    50                  55                  60

Val Lys Tyr Leu Arg Leu Gly Gly Asn Asn Leu Arg Asp Ile Ser Ala
65                  70                  75                  80

Leu Glu Lys Leu Thr Ser Leu Thr Tyr Leu Ile Leu Thr Gly Asn Gln
                85                  90                  95

Leu Gln Ser Leu Pro Asn Gly Val Phe Asp Lys Leu Thr Gln Leu Lys
            100                 105                 110

Glu Leu Val Leu Val Glu Asn Gln Leu Gln Ser Leu Pro Asp Gly Val
        115                 120                 125

Phe Asp Lys Leu Thr Lys Leu Thr Tyr Leu Asn Leu Ala His Asn Glu
    130                 135                 140

Leu Gln Ser Leu Pro Lys Gly Val Phe Asp Lys Leu Thr Ser Leu Lys
145                 150                 155                 160

Glu Leu Asp Leu Ser Tyr Asn Gln Leu Lys Arg Val Pro Glu Gly Ala
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 16
<211> LENGTH: 266
<212> TYPE: PRT
<213> ORGANISM: Artificial Sequence
<220> FEATURE:
<223> OTHER INFORMATION: IVLRc-MD-2

<400> SEQUENCE: 16

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Ser Val Thr
            20                  25                  30
```

```
Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
 50                  55                  60

Val Arg Tyr Leu Ala Leu Gly Gly Asn Lys Leu His Asp Ile Ser Ala
 65                  70                  75                  80

Leu Lys Glu Leu Thr Asn Leu Thr Tyr Leu Ile Leu Thr Gly Asn Gln
                 85                  90                  95

Leu Gln Ser Leu Pro Asn Gly Val Phe Asp Lys Leu Thr Asn Leu Lys
            100                 105                 110

Glu Leu Val Leu Glu Asn Gln Leu Gln Ser Leu Pro Asp Gly Val
        115                 120                 125

Phe Asp Lys Leu Thr Asn Leu Thr Tyr Leu Asn Leu Ala His Asn Gln
130                 135                 140

Leu Gln Ser Leu Pro Lys Gly Val Phe Asp Lys Leu Thr Asn Leu Thr
145                 150                 155                 160

Glu Leu Asp Leu Ser Tyr Asn Gln Leu Gln Ser Leu Pro Glu Gly Val
                165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
        195                 200                 205

Tyr Ile Trp Leu His Asp Asn Pro Trp Asp Cys Thr Cys Pro Gly Ile
    210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
                245                 250                 255

Lys Pro Val Arg Ser Ile Ile Cys Pro Thr
            260                 265

<210> SEQ ID NO 17
<211> LENGTH: 290
<212> TYPE: PRT
<213> ORGANISM: Artificial Sequence
<220> FEATURE:
<223> OTHER INFORMATION: IVLRn5-MD-2

<400> SEQUENCE: 17

Glu Thr Ile Thr Val Ser Thr Pro Ile Lys Gln Ile Phe Pro Asp Asp
1               5                  10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Thr Ile Gln Ala
        35                  40                  45

Met Glu Ser Asp Ile Lys Ser Val Gln Gly Ile Gln Tyr Leu Pro Asn
 50                  55                  60

Val Lys Asn Leu Asp Leu Ser Phe Asn Asn Leu Arg Asp Ile Ser Ala
 65                  70                  75                  80

Leu Glu Lys Leu Thr Asn Leu Thr Val Leu Asp Leu Ser Arg Asn Gln
                 85                  90                  95

Leu Gln Ser Leu Pro Asn Gly Val Phe Asp Lys Leu Thr Ser Leu Thr
            100                 105                 110

Tyr Leu Ile Leu Thr Gly Asn Gln Leu Gln Ser Leu Pro Asn Gly Val
        115                 120                 125
```

```
Phe Asp Lys Leu Thr Gln Leu Lys Glu Leu Val Leu Glu Asn Gln
            130                 135                 140
Leu Gln Ser Leu Pro Asp Gly Val Phe Asp Lys Leu Thr Lys Leu Thr
145                 150                 155                 160
Tyr Leu Asn Leu Ala His Asn Glu Leu Gln Ser Leu Pro Lys Gly Val
                165                 170                 175
Phe Asp Lys Leu Thr Ser Leu Lys Glu Leu Asp Leu Ser Tyr Asn Gln
            180                 185                 190
Leu Lys Arg Val Pro Glu Gly Ala Phe Asp Lys Leu Thr Gln Leu Lys
        195                 200                 205
Asp Leu Arg Leu Tyr Gln Asn Gln Leu Lys Ser Val Pro Asp Gly Val
    210                 215                 220
Phe Asp Arg Leu Thr Ser Leu Gln Tyr Ile Trp Leu His Asp Asn Pro
225                 230                 235                 240
Trp Asp Cys Thr Cys Pro Gly Ile Arg Tyr Leu Ser Glu Trp Ile Asn
                245                 250                 255
Lys His Ser Gly Val Val Arg Asn Ser Ala Gly Ser Val Ala Pro Asp
            260                 265                 270
Ser Ala Lys Cys Ser Gly Ser Gly Lys Pro Val Arg Ser Ile Ile Cys
        275                 280                 285
Pro Thr
    290

<210> SEQ ID NO 18
<211> LENGTH: 290
<212> TYPE: PRT
<213> ORGANISM: Artificial Sequence
<220> FEATURE:
<223> OTHER INFORMATION: IVLRc5-MD-2

<400> SEQUENCE: 18

Glu Thr Ile Thr Val Ser Thr Pro Ile Lys Gln Ile Phe Pro Asp Asp
1               5                   10                  15
Ala Phe Ala Glu Thr Ile Lys Ala Asn Leu Lys Lys Lys Ser Val Thr
                20                  25                  30
Asp Ala Val Thr Gln Asn Glu Leu Asn Ser Ile Asp Thr Ile Gln Ala
            35                  40                  45
Met Glu Ser Asp Ile Lys Ser Val Gln Gly Ile Gln Tyr Leu Pro Asn
        50                  55                  60
Val Arg Asn Leu Asp Leu Ser Phe Asn Lys Leu His Asp Ile Ser Ala
65                  70                  75                  80
Leu Lys Glu Leu Thr Asn Leu Thr Val Leu Asp Leu Ser Arg Asn Gln
                85                  90                  95
Leu Gln Ser Leu Pro Asn Gly Val Phe Asp Lys Leu Thr Asn Leu Thr
            100                 105                 110
Tyr Leu Ile Leu Thr Gly Asn Gln Leu Gln Ser Leu Pro Asn Gly Val
        115                 120                 125
Phe Asp Lys Leu Thr Asn Leu Lys Glu Leu Val Leu Glu Asn Gln
    130                 135                 140
Leu Gln Ser Leu Pro Asp Gly Val Phe Asp Lys Leu Thr Asn Leu Thr
145                 150                 155                 160
Tyr Leu Asn Leu Ala His Asn Gln Leu Gln Ser Leu Pro Lys Gly Val
                165                 170                 175
Phe Asp Lys Leu Thr Asn Leu Thr Glu Leu Asp Leu Ser Tyr Asn Gln
            180                 185                 190
```

```
Leu Gln Ser Leu Pro Glu Gly Val Phe Asp Lys Leu Thr Gln Leu Lys
        195                 200                 205

Asp Leu Arg Leu Tyr Gln Asn Gln Leu Lys Ser Val Pro Asp Gly Val
    210                 215                 220

Phe Asp Arg Leu Thr Ser Leu Gln Tyr Ile Trp Leu His Asp Asn Pro
225                 230                 235                 240

Trp Asp Cys Thr Cys Pro Gly Ile Arg Tyr Leu Ser Glu Trp Ile Asn
                245                 250                 255

Lys His Ser Gly Val Val Arg Asn Ser Ala Gly Ser Val Ala Pro Asp
                260                 265                 270

Ser Ala Lys Cys Ser Gly Ser Gly Lys Pro Val Arg Ser Ile Ile Cys
        275                 280                 285

Pro Thr
    290

<210> SEQ ID NO 19
<211> LENGTH: 266
<212> TYPE: PRT
<213> ORGANISM: Artificial Sequence
<220> FEATURE:
<223> OTHER INFORMATION: IVLRc
<220> FEATURE:
<221> NAME/KEY: MISC_FEATURE
<222> LOCATION: (88)..(89)
<223> OTHER INFORMATION: Xaa is any amino acid
<220> FEATURE:
<221> NAME/KEY: MISC_FEATURE
<222> LOCATION: (91)..(91)
<223> OTHER INFORMATION: Xaa is any amino acid
<220> FEATURE:
<221> NAME/KEY: MISC_FEATURE
<222> LOCATION: (93)..(94)
<223> OTHER INFORMATION: Xaa is any amino acid
<220> FEATURE:
<221> NAME/KEY: MISC_FEATURE
<222> LOCATION: (102)..(102)
<223> OTHER INFORMATION: Xaa is any amino acid
<220> FEATURE:
<221> NAME/KEY: MISC_FEATURE
<222> LOCATION: (112)..(113)
<223> OTHER INFORMATION: Xaa is any amino acid
<220> FEATURE:
<221> NAME/KEY: MISC_FEATURE
<222> LOCATION: (115)..(115)
<223> OTHER INFORMATION: Xaa is any amino acid
<220> FEATURE:
<221> NAME/KEY: MISC_FEATURE
<222> LOCATION: (117)..(118)
<223> OTHER INFORMATION: Xaa is any amino acid
<220> FEATURE:
<221> NAME/KEY: MISC_FEATURE
<222> LOCATION: (126)..(126)
<223> OTHER INFORMATION: Xaa is any amino acid
<220> FEATURE:
<221> NAME/KEY: MISC_FEATURE
<222> LOCATION: (136)..(137)
<223> OTHER INFORMATION: Xaa is any amino acid
<220> FEATURE:
<221> NAME/KEY: MISC_FEATURE
<222> LOCATION: (139)..(139)
<223> OTHER INFORMATION: Xaa is any amino acid
<220> FEATURE:
<221> NAME/KEY: MISC_FEATURE
<222> LOCATION: (141)..(142)
<223> OTHER INFORMATION: Xaa is any amino acid
<220> FEATURE:
<221> NAME/KEY: MISC_FEATURE
<222> LOCATION: (150)..(150)
<223> OTHER INFORMATION: Xaa is any amino acid
<220> FEATURE:
<221> NAME/KEY: MISC_FEATURE
```

```
<222> LOCATION: (160)..(161)
<223> OTHER INFORMATION: Xaa is any amino acid
<220> FEATURE:
<221> NAME/KEY: MISC_FEATURE
<222> LOCATION: (163)..(163)
<223> OTHER INFORMATION: Xaa is any amino acid
<220> FEATURE:
<221> NAME/KEY: MISC_FEATURE
<222> LOCATION: (165)..(166)
<223> OTHER INFORMATION: Xaa is any amino acid
<220> FEATURE:
<221> NAME/KEY: MISC_FEATURE
<222> LOCATION: (174)..(174)
<223> OTHER INFORMATION: Xaa is any amino acid

<400> SEQUENCE: 19
```

Glu Thr Ile Thr Val Ser Thr Pro Ile Lys Gln Ile Phe Pro Asp Asp
1               5                   10                  15

Ala Phe Ala Glu Thr Ile Lys Ala Asn Leu Lys Lys Lys Ser Val Thr
            20                  25                  30

Asp Ala Val Thr Gln Asn Glu Leu Asn Ser Ile Asp Gln Ile Ile Ala
        35                  40                  45

Asn Asn Ser Asp Ile Lys Ser Val Gln Gly Ile Gln Tyr Leu Pro Asn
50                  55                  60

Val Arg Tyr Leu Ala Leu Gly Gly Asn Lys Leu His Asp Ile Ser Ala
65                  70                  75                  80

Leu Lys Glu Leu Thr Asn Leu Xaa Xaa Leu Xaa Leu Xaa Xaa Asn Gln
            85                  90                  95

Leu Gln Ser Leu Pro Xaa Gly Val Phe Asp Lys Leu Thr Asn Leu Xaa
            100                 105                 110

Xaa Leu Xaa Leu Xaa Xaa Asn Gln Leu Gln Ser Leu Pro Xaa Gly Val
        115                 120                 125

Phe Asp Lys Leu Thr Asn Leu Xaa Xaa Leu Xaa Leu Xaa Xaa Asn Gln
130                 135                 140

Leu Gln Ser Leu Pro Xaa Gly Val Phe Asp Lys Leu Thr Asn Leu Xaa
145                 150                 155                 160

Xaa Leu Xaa Leu Xaa Xaa Asn Gln Leu Gln Ser Leu Pro Xaa Gly Val
            165                 170                 175

Phe Asp Lys Leu Thr Gln Leu Lys Asp Leu Arg Leu Tyr Gln Asn Gln
            180                 185                 190

Leu Lys Ser Val Pro Asp Gly Val Phe Asp Arg Leu Thr Ser Leu Gln
            195                 200                 205

Tyr Ile Trp Leu His Asp Asn Pro Trp Asp Cys Thr Cys Pro Gly Ile
        210                 215                 220

Arg Tyr Leu Ser Glu Trp Ile Asn Lys His Ser Gly Val Val Arg Asn
225                 230                 235                 240

Ser Ala Gly Ser Val Ala Pro Asp Ser Ala Lys Cys Ser Gly Ser Gly
            245                 250                 255

Lys Pro Val Arg Ser Ile Ile Cys Pro Thr
            260                 265

```
<210> SEQ ID NO 20
<211> LENGTH: 12
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (1)..(1)
<223> OTHER INFORMATION: Xaa is a hydrophobic amino acid (A, G, F, Y, L,
```

```
        I, V, W)
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (4)..(4)
<223> OTHER INFORMATION: Xaa is a hydrophobic amino acid (A, G, F, Y, L,
        I, V, W)
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (7)..(7)
<223> OTHER INFORMATION: Xaa is a hydrophobic amino acid (A, G, F, Y, L,
        I, V, W)
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (9)..(9)
<223> OTHER INFORMATION: Xaa is a hydrophobic amino acid (A, G, F, Y, L,
        I, V, W)
<220> FEATURE:
<221> NAME/KEY: MISC_FEATURE
<222> LOCATION: (10)..(11)
<223> OTHER INFORMATION: Xaa is any amino acid
<220> FEATURE:
<221> NAME/KEY: MISC_FEATURE
<222> LOCATION: (12)..(12)
<223> OTHER INFORMATION: Xaa is N, Q, S, C or T

<400> SEQUENCE: 20

Xaa Xaa Xaa Xaa Xaa Xaa Xaa Xaa Xaa Xaa Xaa Xaa
1               5                   10

<210> SEQ ID NO 21
<211> LENGTH: 12
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (10)..(11)
<223> OTHER INFORMATION: Xaa is any amino acid

<400> SEQUENCE: 21

Leu Xaa Xaa Leu Xaa Xaa Leu Xaa Leu Xaa Xaa Asn
1               5                   10

<210> SEQ ID NO 22
<211> LENGTH: 24
<212> TYPE: PRT
<213> ORGANISM: Artificial Sequence
<220> FEATURE:
<223> OTHER INFORMATION: Consensus sequence
<220> FEATURE:
```

```
<221> NAME/KEY: MISC_FEATURE
<222> LOCATION: (2)..(3)
<223> OTHER INFORMATION: Xaa is any amino acid
<220> FEATURE:
<221> NAME/KEY: MISC_FEATURE
<222> LOCATION: (5)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (10)..(11)
<223> OTHER INFORMATION: Xaa is any amino acid
<220> FEATURE:
<221> NAME/KEY: MISC_FEATURE
<222> LOCATION: (13)..(13)
<223> OTHER INFORMATION: Xaa is any amino acid
<220> FEATURE:
<221> NAME/KEY: MISC_FEATURE
<222> LOCATION: (15)..(16)
<223> OTHER INFORMATION: Xaa is any amino acid
<220> FEATURE:
<221> NAME/KEY: MISC_FEATURE
<222> LOCATION: (18)..(21)
<223> OTHER INFORMATION: Xaa is any amino acid
<220> FEATURE:
<221> NAME/KEY: MISC_FEATURE
<222> LOCATION: (23)..(24)
<223> OTHER INFORMATION: Xaa is any amino acid

<400> SEQUENCE: 22

Leu Xaa Xaa Leu Xaa Xaa Leu Xaa Leu Xaa Xaa Asn Xaa Leu Xaa Xaa
1               5                   10                  15

Leu Xaa Xaa Xaa Xaa Phe Xaa Xaa
            20

<210> SEQ ID NO 23
<211> LENGTH: 24
<212> TYPE: PRT
<213> ORGANISM: Artificial Sequence
<220> FEATURE:
<223> OTHER INFORMATION: Consensus sequence
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (10)..(11)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is any amino acid

<400> SEQUENCE: 23

Leu Thr Asn Leu Thr Xaa Leu Xaa Leu Xaa Xaa Asn Gln Leu Lys Ser
1               5                   10                  15

Leu Pro Xaa Gly Val Phe Asp Asn
            20

<210> SEQ ID NO 24
<211> LENGTH: 24
<212> TYPE: PRT
<213> ORGANISM: Artificial Sequence
<220> FEATURE:
<223> OTHER INFORMATION: Consensus sequence
```

```
<220> FEATURE:
<221> NAME/KEY: MISC_FEATURE
<222> LOCATION: (6)..(6)
<223> OTHER INFORMATION: Xaa is any amino acid
<220> FEATURE:
<221> NAME/KEY: MISC_FEATURE
<222> LOCATION: (8)..(8)
<223> OTHER INFORMATION: Xaa is any amino acid
<220> FEATURE:
<221> NAME/KEY: MISC_FEATURE
<222> LOCATION: (10)..(11)
<223> OTHER INFORMATION: Xaa is any amino acid
<220> FEATURE:
<221> NAME/KEY: MISC_FEATURE
<222> LOCATION: (19)..(19)
<223> OTHER INFORMATION: Xaa is any amino acid

<400> SEQUENCE: 24

Leu Thr Lys Leu Thr Xaa Leu Xaa Leu Xaa Xaa Asn Gln Leu Gln Ser
1               5                   10                  15

Leu Pro Xaa Gly Val Phe Asp Lys
            20
```

WATER-SOLUBLE POLYPEPTIDES COMPRISED OF REPEAT MODULES, METHOD FOR PREPARING THE SAME AND METHOD FOR A TARGET-SPECIFIC POLYPEPTIDE AND ANALYSIS OF BIOLOGICAL ACTIVITY THEREOF

CROSS REFERENCE TO RELATED APPLICATIONS

This application is a U.S. National Stage Application filed under 35 U.S.C. §371 and claims priority to International Application No. PCT/KR2012/002094, filed Mar. 22, 2012, which application claims priority under 35 U.S.C. §119 to Korean Application No. 10-2011-0025446, filed Mar. 22, 2011, the disclosures of which are incorporated herein by reference.

TECHNICAL FIELD

The present invention relates to a soluble polypeptide comprised of repeat modules. More particularly, the present invention relates to a soluble fusion polypeptide of the N-terminal domain of internalin and LRR (Leucine rich repeat) family protein, a method for preparing the polypeptide, a vector comprising a nucleic acid sequence encoding the polypeptide, a host cell comprising the vector, a method for producing a fusion polypeptide with a solubility and folding by expressing the vector in the host cell, and a method for improving the solubility and folding of the fusion polypeptide. Further, the present invention relates to a method for preparing the polypeptide bound with specific target and analyzing the efficacy of the soluble polypeptide.

BACKGROUND

Proteins are the substances responsible for the modulation of numerous biological processes in living organisms, and understanding their intrinsic properties and the study and modulation of their interactions with other substances has become more important for developing treatments for various diseases. One of the major obstacles to the investigation and utilization of proteins is mass-production of proteins. In particular, a bacterial system useful for mass-production of proteins cannot be applied to many human-derived proteins, and thus animal cells or plant cells are currently used for the production of human-derived proteins despite the low production yield.

Repeat proteins refer to all proteins of specific unit modules. Particularly, LRR (Leucine Rich Repeat) family proteins refer to consisting of an assembly of diverse leucine-rich repeat modules at defined positions. LRR family proteins contain an N-terminal region, a variable number of repeat modules, and a C-terminal region to forma stable structure. The repeat module of LRR family proteins has the following characteristics; (1) it has at least one repeat module; (2) the repeat module consists of 20 to 30 amino acids; (3) the repeat module has a conserved pattern of "LxxLxxLxLxxN" (SEQ ID NO:20 and 21), wherein L represents a hydrophobic amino acid such as alanine, glycine, phenylalanine, tyrosine, leucine, isoleucine, valine, and tryptophane, N represents asparagine, glutamine, serine, cysteine or threonine, and X represents any amino acid. LRR family protein further has the characteristics of varying the number of repeat modules and the shape of the C-terminal region, enlarging the binding area with other proteins, and making a new binding site. Representative examples of LRR family protein include Toll-Like Receptor protein (TLR) involved in human immunity, Variable Lymphocyte Receptor (VLR) involved in hagfish immunity, Ribonuclease Inhibitor protein (RI) or the like. Each of them is utilized in immunological or molecular biological studies, and they are usually commercialized and utilized in the studies by production in insect or animal cells, isolation of VLR from hagfish after injection of antigens, or direct extraction of RI from placenta. One more example is the use of VLR that is produced after refolding of inclusion bodies expressed in *E. coli*. It is believed that such difficulties in mass-production of soluble LRR family proteins in bacteria such as *E. coli* may be attributed to obstruction of consecutive hydrophobic residues of LRR family protein in the expression of the soluble form. VLR proteins are involved in the immunity of jawless fish, and are similar to antibodies in constitution and utilization. Thus, if their mass-production is possible, they are expected to possess broad applicability like antibodies. In addition, it is known that LRR family proteins are involved in diverse physiological processes such as signal transduction, cell cycle regulation, apoptosis and immune response. Thus, there is an urgent need to develop a technique capable of mass-producing LRR family proteins in a soluble form in host cells such as *E. coli*, because the technique would make it possible to extend the applications of LRR family protein in the biological and medical fields.

Meanwhile, a novel therapeutic protein which binds with a specific target, for example MD-2 (Myeloid differentiation protein-2) protein which is used as an agent for sepsis, could be prepared by various methods using LRR family protein. The preparation method for the polypeptide bound with a specific target is effectively accomplished by designing is based on a structure.

Sepsis is a highly fatal disease caused by immune hypersensitivity reactions due to bacterial infection, which is characterized by thrombosis, multiple organ dysfunction syndrome, and high mortality (60%). The most common cause of sepsis is lipopolysaccharide (LPS) which is the major component of the outer membrane of Gram-negative bacteria, and the immune responses are known to be initiated by recognition of bacterial LPS infected in blood by immune cells.

TLRs (toll-like receptors), found on the surface of human immune cells, play a major role in the induction of innate immunity, and LPS initiates signal transduction through TLR4 among TLRs, which results in the release of cytokines and the induction of immune responses. This immune response is a normal event in the body, but progression of immune hypersensitivity reactions in people whose immune system is weakened by disease or extreme stress may lead to severe sepsis. However, LPS does not directly bind to the TLR4 receptor which is one of the innate immune receptors, and LPS binds to a TLR4/MD-2 complex by mediation of MD-2 (Myeloid differentiation protein-2) to initiate the signal transduction. Therefore, recent studies have been made to develop a therapeutic agent for sepsis, which targets TLR4, MD-2, or TLR4/MD-2 complex to block the LPS signal transduction.

Currently only one drug, Xigris (Eli Lilly), is FDA-approved specifically for sepsis therapy, and is a recombinant version of naturally occurring APC (activated protein C) that has an anti-thrombotic effect. Xigris is anticipated to save approximately 15% of the lives of patients with the most severe forms of sepsis. In addition, eritoran was developed by Eisai (Japan) for the purpose of treating sepsis, which is similar to LPS in chemical structure, thereby binding to MD-2 competitively, and it was undergoing phase III clinical trials in the end of 2009. Many other therapeutic agents including antibodies, developed by numerous pharmaceutical companies, have undergone clinical trials. Unfortunately, most of them show no effect or very low effects, thereby bringing no positive outcomes (Triantafilou et al., Expert Rev. Mol. Med. 24; 6(4):1-18, 2004).

Meanwhile, each of the proteins involved in LPS signal transduction, LBP, CD14, MD-2, and soluble TLR4 (sTLR4), are known to inhibit the LPS signal transduction, and thus they are used for the development of a promising therapeutic agent for sepsis. The sTLR4/MD-2 complex is known to show very excellent inhibitory effect on the LPS signal transduction. MD-2 singly forms a non-functional complex, but binding of MD-2 with sTLR4 forms a stable structure, resulting in competition for LPS binding between sTLR4/MD-2 complex and TLR4/MD-2 complex present on the surface of immune cells (Mitsuzawa et al., J. Immunolo., 177:8133-8139, 2006; Brandl et al., J. Endotoxin Res., 11:197-206, 2005). In addition, each binding affinity (Kd) of CD14, MD-2, and TLR4/MD-2 complex for LPS is reported to be 30 nM, 65 nM, and 3 nM, respectively, and the higher inhibitory effect of sTLR4/MD-2 complex on LPS than CD14 and MD-2 is attributed to such difference in the binding affinity (Akashi et al., J. Exp. Med., 198(7):1035-1042, 2003).

However, there is a drawback in that the high molecular weight and insoluble expression of cell membrane protein make it difficult to produce sTLR4. In order to solve this problem, treatment of experimental animals (mouse) with a TV3 protein alone (without MD-2), which was prepared by fusion of a hagfish variable lymphocyte receptor (VLR) with the MD-2 binding site of TLR4, showed inhibitory effects on sepsis (PLoS ONE, 4:e7403, 2009). The TV3 fusion protein is a protein therapeutic agent that is prepared by a hybrid LRR technique of assembling LRR (leucine rich repeat) family proteins such as TLR4, and the hybrid LRR technique is a promising method in development of novel protein scaffolds as alternatives to antibodies as well as in the development of therapeutic agents for sepsis.

Meanwhile, sepsis results from excessive immune response initiated by signal transduction of the innate immune system. Thus, therapeutic agents developed for the treatment of sepsis are required to have a rapid, immune cell-based assay system. That is, protein drugs showing inhibitory effects on sepsis are required to have a cell-based assay system for LPS-induced immune response. Therefore, the present invention intended to develop a cell-based assay system for monitoring the LPS blocking activity of the LRR protein drugs by introduction of an NF-κB dependant firefly luciferase gene into the HEK293 cell line. The present invention also intended to develop a cell-based assay system for monitoring the LPS blocking activity of the protein drugs by analyzing cytokines secreted from the LPS-treated, macrophage-differentiated THP-1. However, there is a problem in that both of the above cell lines showed no LPS blocking activity when sTLR4, TV3, or a protein drug prepared by the hybrid LRR technique is used alone (without MD-2), even though they express TLR4 and MD-2 required for LPS signal transduction.

DISCLOSURE

Technical Problem

The present inventors have made many efforts to develop a technique capable of producing a large amount of soluble LRR family proteins comprised of repeat modules in host cells such as *E. coli*. As a result, they found that LRR family proteins can be stably mass-produced as soluble forms in *E. coli* by fusion of LRR family proteins with the N-terminal domain of internalin, thereby completing the present invention. The present inventors named the soluble LRR family proteins "Repebody", since they have characteristics similar to antibodies.

Meanwhile, the present inventors prepared Repebody bound with specific targets, and the Repebody could be used in analysis for immunity, diagnosing and imaging diseases, targeted delivery for drugs, and as a protein treatment agent. The present inventors prepared Repebody which binds with MD-2, and developed a method for analysis of the biological activity thereof. The present inventors have made many efforts to develop a method for screening protein drugs blocking the LPS signal transduction and a method for rapidly analyzing their effects. They found that addition of purified MD-2 allows stable complex formation of MD-2 with sTLR4 and TV3, or LRR protein, leading to LPS capture and reduction of signal transduction, and thus a cell-based assay system provided with purified MD-2 is only effective for the analysis and exploration of protein drugs, thereby completing the present invention.

Technical Solution

An object of the present invention is to provide a soluble fusion polypeptide prepared by fusion of the N-terminal domain of internalin protein and LRR (Leucine rich repeat) family protein.

Another object of the present invention is to provide a method for preparing the fusion polypeptide, comprising the steps of (a) ranking module pairs based on similarity scores in repeat modules between the internalin protein and the LRR family protein; (b) selecting modules having high similarity scores from the aligned repeat modules of step (a); (c) positioning the repeat modules of internalin protein at the N-terminus and the repeat modules of LRR family protein at the C-terminus in the modules selected in step (b); (d) calculating a binding energy of the fusion polypeptides designed in step (c) to select a fusion polypeptide showing an optimal binding stability between internalin protein and LRR family protein; and (e) modifying surface hydrophilic residues of the repeat modules of internalin protein contained in the fusion polypeptide selected in step (d) so as to determine a final sequence alignment having a minimum energy function value.

Still another object of the present invention is to provide a vector comprising a nucleic acid sequence encoding the soluble fusion polypeptide, or a host cell comprising the vector.

Still another object of the present invention is to provide a method for producing a fusion polypeptide with improved solubility and folding, comprising the steps of (a) preparing a vector comprising a nucleic acid sequence encoding the soluble fusion polypeptide; (b) introducing the prepared vector into host cells; and (c) recovering the fusion polypeptide from the host cells.

Still another object of the present invention is to provide a method for improving the solubility and folding of the fusion polypeptide, comprising the steps of (a) preparing a vector comprising a nucleic acid sequence encoding the soluble fusion polypeptide; (b) introducing the prepared vector into host cells; and (c) expressing the fusion polypeptide in the host cells.

Still another object of the present invention is to provide a method for analyzing the efficacy of the fusion polypeptide used as a therapeutic agent for sepsis capable of blocking the LPS signal transduction, by using a cell-based assay system provided with MD-2.

Advantageous Effects

LRR family proteins, for which there are difficulties in mass-producing by known methods, can be produced in a large amount as a soluble form in bacteria such as E. coli by using the method for producing a large amount of a LRR family protein as a soluble form using a soluble fusion polypeptide that is prepared by fusion of the N-terminal domain of internalin protein and LRR family protein of the present invention. Therefore, the present invention makes it possible to obtain a large amount of LRR family proteins, and thus will greatly contribute to academic research and industrial and medical applications. In addition, the structural-based rational design of the novel polypeptide which binds with a specific target will contribute to academic research and industrial and medical applications.

Moreover, the cell-based assay system according to the present invention binds with MD-2 to maintain structural stability, and thus can be used for the analysis and exploration of LRR family protein which is prepared to capture LPS as a protein drug.

DESCRIPTION OF DRAWINGS

FIG. 1 shows SEQ ID NO: 1, which represents a variant of Agnatha such as Lamprey- and/or hagfish-derived VLR protein having three repeat modules, and has been named Eb8VLRB.59 by the present inventors, in which the signal sequence is shaded, the N-terminus is in the box, three repeat modules are underlined, the C-terminus is double-underlined, and the stalk is in the shaded box;

FIG. 2 shows SEQ ID NO: 2 consisting of 5 repeat modules, and which was named VLR5n by the present inventors, in which the N-terminal signal sequence region and the C-terminal stalk region are deleted, based on SEQ ID NO: 1, and the underlined residues are designed for binding;

FIG. 3 shows SEQ ID NO: 3 consisting of 5 repeat modules by consensus design, and which was named VLR5c by the present inventors, in which repeated sequences in the consensus sequence are underlined and repeat modules are in the box;

FIG. 5 shows SEQ ID NO: 6 representing an InlB-VLR5c fusion protein prepared by fusion of N-terminus of internalin B protein and VLR5c, in which the internalin region is in the box, and the VLR region is in the shaded box;

FIG. 6 shows SEQ ID NO: 7 representing an InlB-VLR5n-Rosseta fusion protein that is prepared by redesigning InlB-VLR5n of SEQ ID NO: 5 using ROSETTADESIGN software, in which the mutated amino acids by ROSETTADESIGN software are underlined;

FIG. 7 shows SEQ ID NO: 8 representing an InlB-VLR5c-Rosseta fusion protein that is prepared by redesigning InlB-VLR5c of SEQ ID NO: 6 using ROSETTADESIGN software, in which the mutated amino acids by ROSETTADESIGN software are underlined;

FIG. 10 shows SEQ ID NO: 9 representing InlB-VLR6n that is prepared by addition of one consensus module of VLR next to internalin, based on InlB-VLR5n-Rosseta of SEQ ID NO: 7, in which internalin is shaded, added module is double-underlined, and VLR region is colored black;

FIG. 11 shows SEQ ID NO: 10 representing InlB-VLR6c that is prepared by addition of one consensus module of VLR next to internalin, based on InlB-VLR5c-Rosseta of SEQ ID NO: 8, in which internalin is shaded, added module is double-underlined, and VLR region is colored black;

FIG. 13 shows SEQ ID NO: 12 representing InlB-VLR-TV3 that is prepared by replacement of hydrophobic amino acids involved in protein stability with consensus sequences;

FIG. 20 shows SEQ ID NO: 14 representing IVLRn that is prepared by fusion of N-terminus of internalin B protein and VLR-derived repeat modules, in which internalin region is shaded, VLR repeat modules are colored black, and C-terminus is in the box;

FIG. 21 shows SEQ ID NO: 15 representing IVLRn-MD2 that is prepared by the replacement of amino acids of repeat modules for binding with MD-2, based on IVLRn, in which internalin region is shaded, VLR repeat modules are colored black, C-terminus is in the box, and the 12 underlined amino acids represent replaced amino acids for binding with MD-2;

FIG. 22 shows SEQ ID NO: 16 representing IVLRc-MD2 that is prepared by replacement of amino acids of repeat modules for binding with MD-2, based on IVLRc, in which internalin region is shaded, VLR repeat modules by consensus design are colored black, C-terminus is in the box, and 12 underlined amino acids represent replaced amino acids for binding with MD-2;

FIG. 23 shows SEQ ID NO: 17 representing IVLRn5-MD2 that is prepared by the addition of one repeat module, based on IVLRn-MD2, in which internalin region is shaded, added VLR repeat module is in the shaded box, naturally occurring VLR repeat modules are colored black, C-terminus is in the box, and the 24 underlined amino acids represent replaced amino acids for binding with MD-2;

FIG. 24 shows SEQ ID NO: 18 representing IVLRc5-MD2 that is prepared by the addition of one repeat module, based on IVLRc-MD2, in which internalin region is shaded, added VLR repeat module is in the shaded box, naturally occurring VLR repeat modules are colored black, C-terminus is in the box, and the 24 underlined amino acids represent replaced amino acids for binding with MD-2;

FIG. 25 shows a sequence that is prepared by the addition of 4 repeat modules, based on consensus sequence, in which internalin region is shaded, repeat modules are colored black, C-terminus is in the box, and x of the repeat module is any amino acid;

BEST MODE

Figure 4:
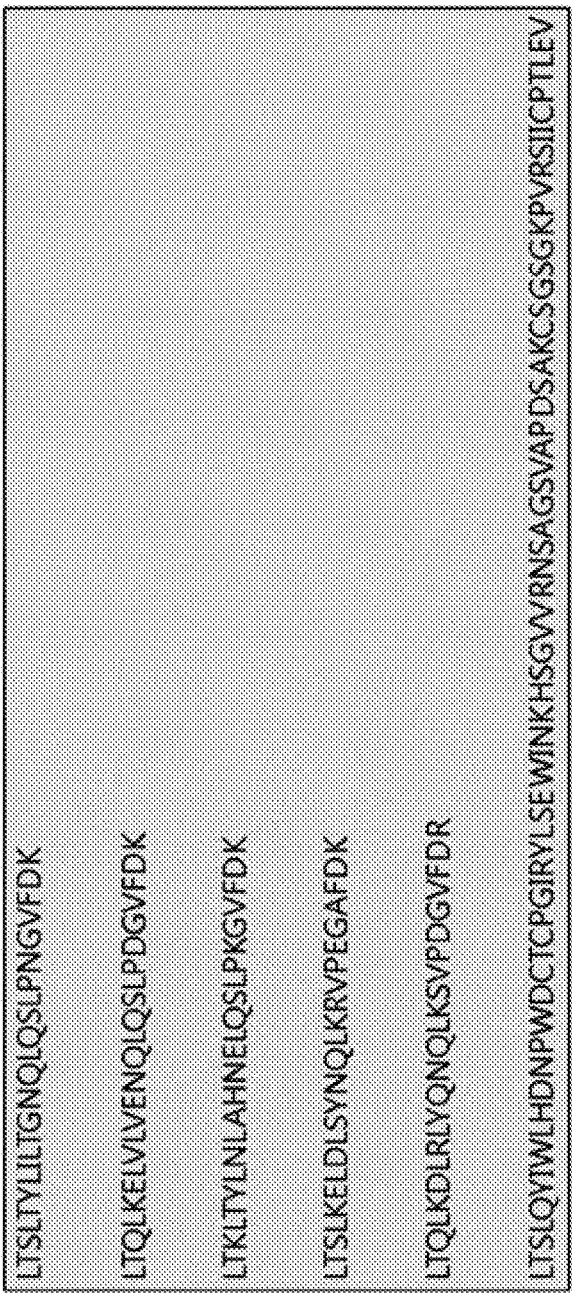
FIG. 4 shows SEQ ID NO: 5 representing an InlB-VLR5n fusion protein prepared by fusion of N-terminus of internalin B protein and VLR5n, in which the internalin region is in the box, and the VLR region is in the shaded box.

In one aspect, the present invention relates to a soluble fusion polypeptide prepared by fusion of the N-terminal domain of internalin protein and LRR (Leucine-rich repeat) family protein.

As used herein, the term "internalin protein" belongs to a family of LRR proteins, found in *Listeria*. It is known to be stably expressed in microorganisms due to its N-terminal structure differents from other LRR family proteins, which have hydrophobic cores distributed throughout the molecule. It is known that the N-terminal structure of internalin protein involved in the folding of repeat modules is derived from microorganisms, and has a more stable alpha helical structure, resulting in its stable expression in microorganisms. The internalin protein used in the fusion of the present invention includes any internalin protein without limitation, as long as it is expected to have a similar N-terminal structure and play an important role in protein folding. Examples thereof include internalin A, internalin B, internalin C, internalin H, and internalin J and preferably internalin B. Internalin A to J are very similar to each other in their structure. With respect to RMSD (Root mean square deviation) values with the N-terminus of internalin B protein according to structural alignment, internalin A (36 to 115) has 0.6, internalin C (36 to 115) has 0.793, internalin H (36 to 115) has 0.619, and internalin J (57 to 131) has 0.862, indicating that they are very similar to each other in structure.

As used herein, the term "N-terminus of internalin protein" means an N-terminus of internalin protein that is required for soluble expression and folding of the protein, and means an alpha helical capping motif and a repeat module of internalin protein. The N-terminus of internalin protein includes any N-terminus of internalin protein without limitation, as long as it is required for soluble expression and folding of the protein. Examples thereof may include an alpha helical capping motif "ETITVSTPIKQIFPDDAFAE-TIKANLKKKSVTDAVTQNE" (SEQ ID NO:4 from amino acid 1 to 39) and a repeat module. Preferably, the repeat module may include the pattern of "LxxLxxLxLxxN" (SEQ ID NO:20 and 21), wherein L represents alanine, glycine, phenylalanine, tyrosine, leucine, isoleucine, valine, or tryptophane; N represents asparagine, glutamine, serine, cysteine or threonine; and X represents any hydrophilic amino acid. The N-terminus of internalin protein may have SEQ ID NO: 13, but an N-terminus having high structural similarity can be selected depending on the type of LRR family protein to be fused. It is possible to modify the amino acids of the corresponding module using the most stable amino acids selected by calculation of binding energy, etc.

As used herein, the term "LRR (Leucine-rich repeat) family protein" refers to all proteins consisting of an assembly of diverse leucine-rich repeat modules at defined positions, and has the following characteristics: i) it has at least one LRR repeat module; (ii) the LRR repeat module consists of 20 to 30 amino acids; (iii) the LRR repeat module has a conserved pattern of "LxxLxxLxLxxN" (SEQ ID NO:20 and 21), wherein L represents a hydrophobic amino acid such as alanine, glycine, phenylalanine, tyrosine, leucine, isoleucine, valine, and tryptophane, N represents asparagine, glutamine, serine, cysteine or threonine, and X represents any amino acid; and iv) the LRR family protein has a horseshoe like tertiary structure. The LRR family protein of the present invention may include those having previously known sequences or being found in vivo using newly induced mRNA or cDNA, as well as all variants having naturally unknown sequences and newly designed scaffold of repeat modules by consensus design, etc., but is not limited thereto. Examples thereof may include Variable Lymphocyte Receptor (VLR), Toll-Like Receptor (TLR), TV3 protein, U2A, and Ribonuclease Inhibitor (RI). According to one embodiment of the present invention, when the fusion protein of N-terminus of internalin B protein and VLR protein was prepared and used, the production amount was greatly improved as compared to before the fusion (FIG. 9), suggesting that the fusion polypeptide of the present invention can be highly expressed in *E. coli* as a soluble form.

In one preferred embodiment, the LRR family protein is not limited in the number of repeat modules, as long as the soluble fusion polypeptide is stably expressed, and preferably is from 1 to 9. The number of LRR repeat modules may include naturally occurring modules and artificially added or deleted modules, as long as the fusion polypeptide retains the scaffold. According to one embodiment of the present invention, even though the number of repeat modules of the internalin-VLR fusion protein is increased, high expression of the soluble form was observed in *E. coli* (FIG. 12).

In one preferred embodiment, the N-terminus of internalin protein and LRR family protein may be linked with each other via a linker, and the linker may be repeat modules of LRR family protein different from the LRR family protein to be fused. The linker may be VLR repeat modules, but is not limited thereto. In this regard, if the soluble fusion polypeptide is not expressed in a large amount in bacteria such as *E. coli* because of a lack of stability due to a difference in the number of amino acids within repeat modules between the LRR family protein and the N-terminus of internalin protein, the LRR repeat modules of LRR family protein having the repeat modules consisting of the similar number of amino acids are used as a linker, leading to formation of a stable structure and high expression of a soluble form.

In one preferred embodiment, the LRR family protein may be modified by substitution, deletion or insertion of amino acids, in order that the fusion polypeptide is capable of binding with a target protein.

As used herein, the term "fusion polypeptide", "fusion protein" and "binding protein" are interchangeable, and they are prepared by fusion of modules showing high structural similarity in repeat modules between the N-terminus of internalin protein and the LRR family protein. They also include fusion polypeptides that have modification of a part of the amino acids to have the highest stability, determined by calculation of binding energy of repeat modules between the internalin protein and the LRR family protein. All fusion polypeptides can be included without limitation, as long as they are stably and excessively expressed in soluble forms in *E. coli*, and for example, may be a fusion polypeptide having an amino acid sequence represented by SEQ ID NO: 7, SEQ ID NO: 8, SEQ ID NO: 9, SEQ ID NO: 10, SEQ ID NO: 12, SEQ ID NO: 15, SEQ ID NO: 16, SEQ ID NO: 17, or SEQ ID NO: 18.

The fusion polypeptide may be preferably a fusion polypeptide specifically binding to MD-2 (Myeloid differentiation protein-2) protein, in which the fusion polypeptide is prepared by fusion of N-terminus of internalin B protein, modified repeat modules of VLR (Variable Lymphocyte Receptor) protein, and C-terminus of VLR protein.

The N-terminus of internalin B protein may be selected from N-terminus having high structural similarity depending on the type of VLR (Variable Lymphocyte Receptor) to be fused. The most stable amino acids are determined by calculation of binding energy, and used for amino acid modification of the corresponding modules.

As used herein, the term "VLR (Variable Lymphocyte Receptor) protein" is one of LRR family proteins, expressed in hagfish or lamprey, and plays a role in hagfish or lamprey immunity. It has attracted much attention as an antigen binding protein. The fusion polypeptide of the N-terminus of internalin B protein and VLR protein shows high soluble expression, compared to the VLR protein alone, and thus it is useful for the preparation of novel protein drugs. According to one embodiment of the present invention, the fusion polypeptide showed a greatly increased expression level of 60 mg/L, which was 20 times higher than the VLR protein alone (3 mg/L) (see Example 5-2). Such improvement in the expression level suggests that the use of the polypeptide of the present invention creates an economic advantage. The improvement in expression level by using the fusion polypeptide prepared by fusion of the internalin B protein and the VLR protein was first developed by the present inventors.

As used herein, the term "modified repeat modules of VLR protein" means a graft of TV3 amino acids involved in binding with MD-2 into leucine rich repeat modules consisting of 24 residues of VLR protein. The repeat modules have a conserved pattern of "LxxLxxLxLxxN" (SEQ ID NO:20 and 21), wherein L represents a hydrophobic amino acid such as alanine, glycine, phenylalanine, tyrosine, leucine, isoleucine, valine, and tryptophane, N represents asparagine, glutamine, serine, cysteine or threonine, and X represents any amino acid. The LRR family protein of the present invention may include those having previously known sequences or being found in vivo using newly induced mRNA or cDNA, as well as all variants having naturally unknown sequences and newly designed scaffold of repeat modules by consensus design, etc.

In one preferred embodiment, the amino acid sequence of the repeat modules in the fusion polypeptide of the present invention complies with the definition of LRR family, but the modified repeat modules of VLR protein are combinations of repeat modules of naturally occurring sequences or combinations of repeat modules of sequences that are designed to have high stability by consensus design. Preferably, they include those that are designed by consensus design so as to retain structurally important amino acids and have various amino acids in the variable region. The fusion polypeptide is able to specifically bind to MD-2 protein, and preferably a fusion polypeptide of SEQ ID NO: 15, 16, 17, or 18 (FIGS. 21 to 24). With respect to the objects of the present invention, it is apparent that fusion polypeptides having substitution, deletion, or addition of one or more amino acids in any one sequence of SEQ ID NOs: 15 to 18 are also included in the scope of the present invention, as long as they retain the activity of specifically binding to MD-2 protein.

Figure 17:
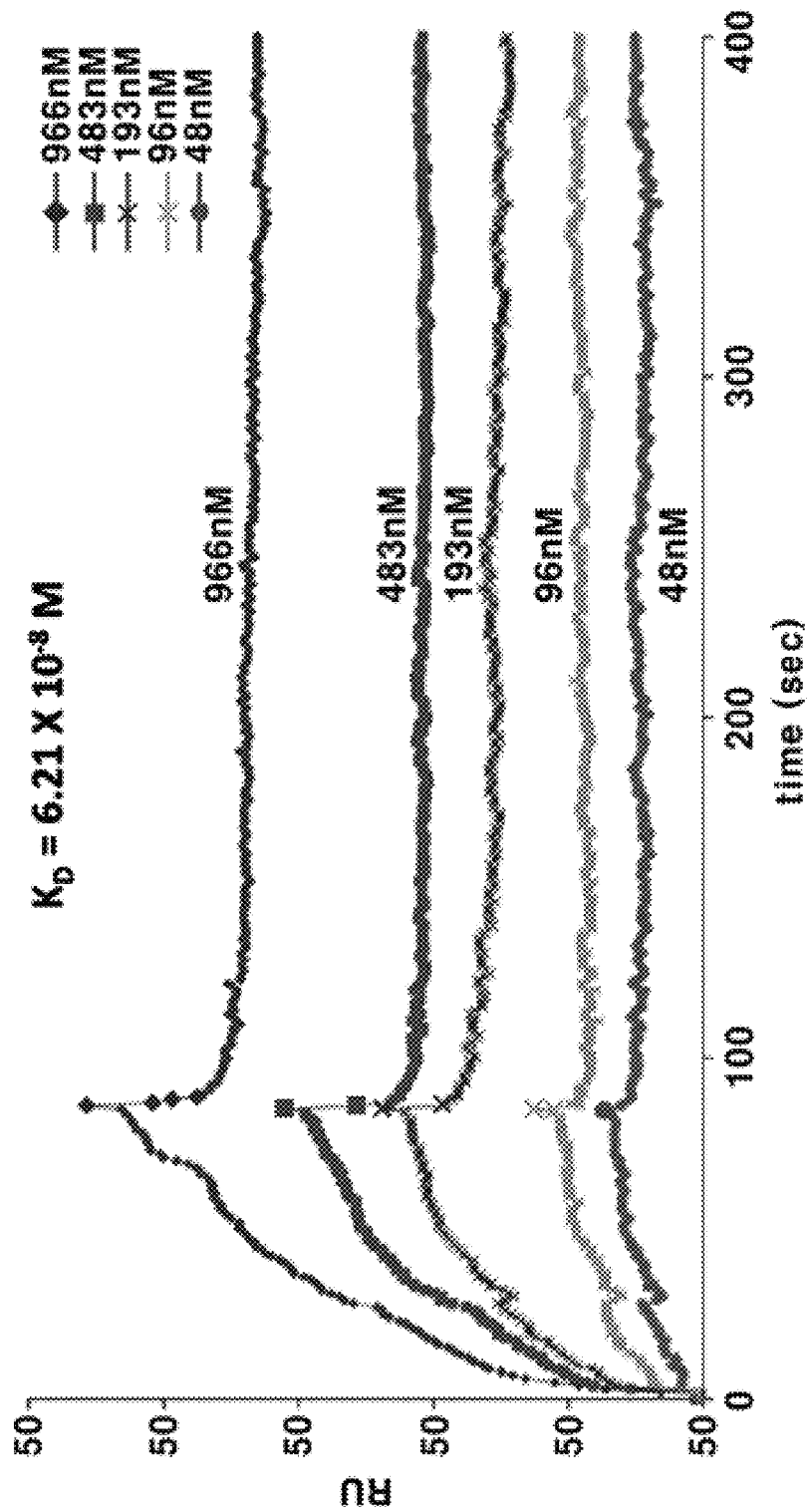
FIG. 17 shows the MD-2 binding affinity of IVLRc-MD2 (SEQ ID NO: 16) prepared based on consensus sequences, examined by SPR.
Figure 18:
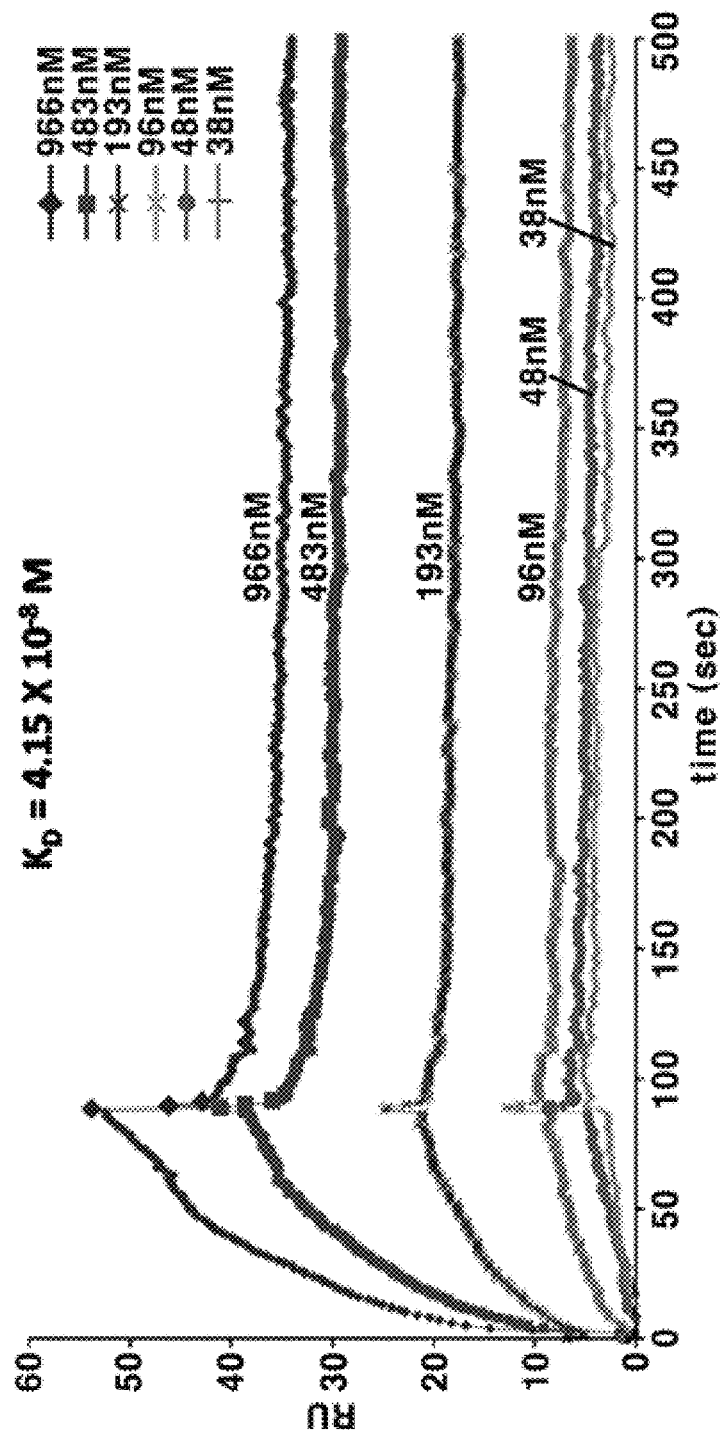
FIG. 18 shows the MD-2 binding affinity of IVLRn-MD2 (SEQ ID NO: 15) prepared using naturally occurring repeat modules, examined by SPR.
Figure 19:
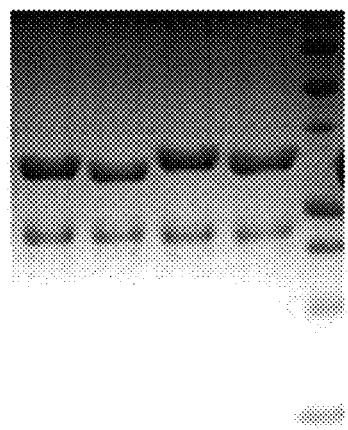
FIG. 19 shows the MD-2 binding affinity of the proteins having 4 repeat modules (IVLRc-MD2 and IVLRn-MD2, SEQ ID NO: 15 and SEQ ID NO: 16), and the proteins having 5 repeat modules (IVLRc5-MD2 and IVLRn5-MD2, SEQ ID NO: 17 and SEQ ID NO: 18), in which all proteins designed by using naturally occurring sequences and consensus sequences showed binding affinity, and when each protein was mixed with MD-2, Lane 1: IVLRn-MD2, Lane 2: IVLRc-MD2, Lane 3: IVLRn5-MD2, Lane 4: IVLRc5-MD2, all proteins were isolated as MD-2-binding forms (2 bands), Lane 5: standard marker.

According to one embodiment of the present invention, a binding affinity ($K_D$) of the fusion polypeptide of SEQ ID NO: 15 for MD-2 was $4.15 \times 10^{-8}$ M (FIG. 18), and that of the fusion polypeptide of SEQ ID NO: 16 for MD-2 was $6.21 \times 10^{-8}$ M (FIG. 17). There was no difference, compared to that ($7.6 \times 10^{-8}$ M) of TV3 that is known to bind with MD-2. Those of SEQ ID NOs: 17 and 18, which have one additional repeat module, also maintain the binding affinity for MD-2 (FIG. 19). These results demonstrate that the fusion polypeptide specifically binds with MD-2.

As used herein, the term "MD-2 (Myeloid differentiation protein-2) protein" is a glycoprotein capable of binding to LPS (Lipopolysaccharide), and refers to a protein that transfers LPS to TLR-4 (Toll-like receptor-4) present on the surface of immune cells so as to activate the intracellular signal transduction.

Figure 15:
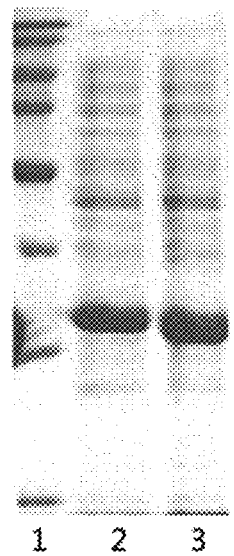
FIG. 15 shows protein expression levels of polypeptide containing naturally occurring VLR repeat modules and polypeptide containing VLR repeat modules having consensus sequences, in which the protein consisting of 4 repeat modules having consensus sequences showed higher protein expression level than the protein consisting of 4 naturally occurring repeat modules, Lane 1 represents standard marker, Lane 2 represents protein containing naturally occurring repeat modules (IVLRn-MD2, SEQ ID NO: 15), and Lane 3 represents protein containing repeat modules having consensus sequences (IVLRc-MD2, SEQ ID NO: 16)

According to one embodiment of the present invention, even though all proteins are equally designed to bind with MD-2, consensus design of repeat modules was shown to increase the solubility and the expression level (FIG. 15).

Preferably, the consensus repeat module having high stability is a repeat module of the following Sequence Formula 1:

[LTNLxxLxLxxNQLQSLPxGVFDK] (SEQ ID NO: 19 from amino acid 132 to 155)      [Sequence Formula 1]

wherein x may be any amino acid. In the VLR repeat module, the consensus residues are fixed, and the variable regions are represented by x, and are preferably important amino acids involved in binding with MD-2 protein.

According to one preferred embodiment, the number of repeat modules of the polypeptide may vary, and naturally the polypeptide has 2 to 9 modules, but is not limited thereto. According to one embodiment of the present invention, even though the number of repeat modules was increased, the binding affinity for MD-2 was maintained, and its own stability was also improved (FIG. 19).

Preferably, various substitutions in the C-terminus of the polypeptide are possible, and in particular, a loop structure frequently used in binding with target materials may vary in its length.

In another aspect, the present invention relates to a method for preparing a soluble fusion polypeptide, comprising the steps of (a) ranking module pairs based on similarity scores in repeat modules between the internalin protein and the LRR family protein; (b) selecting modules having the high similarity scores from the aligned repeat modules of step (a); (c) positioning the repeat modules of internalin protein at the N-terminus and the repeat modules of LRR family protein at the C-terminus in the modules selected in step (b); (d) calculating a binding energy of the fusion polypeptides designed in step (c) to select a fusion polypeptide showing an optimal binding stability between internalin protein and LRR family protein; and (e) modifying surface hydrophilic residues of the repeat modules of internalin protein contained in the fusion polypeptide selected in step (d) so as to determine a final sequence alignment having a minimum energy function value.

In one preferred embodiment, as described above, step (c) may further include a step of adding or removing repeat modules, or a step of linking the internalin protein with the LRR family protein via a linker. The repeat module and linker are the same as described above.

In Step (a) of structurally aligning the repeat modules between the internalin protein and the LRR family protein and step (b) of selecting modules having the high similarity scores from the aligned repeat modules, the proteins are isolated as module pairs and their structural similarity is calculated to select the module pairs having high similarity scores such as RMSD and maintaining the desirable properties. The structural similarity scores may be determined by using a known similarity calculation program protein or a directly designed program, and examples thereof include TM-align (http://zhang.bioinformatics.ku.edu/TM-align/), CE (http://cl.sdsc.edu/), Mammoth (http://ub.cb-m.uam.es/mammoth/pair/index3.php), and DALI (http://ekhidna.biocenter.helsinki.fi/dali_server/start), but are not limited thereto.

In steps (c) and (d), the fusion polypeptide is designed by locating the internalin sequence at the former module, namely, the N-terminus and the LRR family protein at the latter module, namely, the C-terminus, and the binding energy of the designed fusion polypeptide is calculated to select an optimal fusion polypeptide structure. The final structural model can be selected by repeating molecular dynamics simulation and energy stabilization process using the known program such as Modeller (version 9v4).

In step (e) of selecting the final sequence alignment, amino acids having a minimum energy function value are selected using the known program capable of calculating energy function value, and replaced to the surface hydrophilic residues, thereby selecting the final sequence candidate. The program calculating energy function value may be any known program without limitation, and examples thereof include ROSETTADESIGN, FOLDX, GROMACS, and AMBER, but are not limited thereto.

Preferably, step (e) may further include a step of modifying by substitution, deletion or insertion of amino acids, in order that the fusion polypeptide is capable of binding with the target protein.

In still another embodiment, the present invention relates to a vector comprising a nucleic acid sequence encoding the fusion polypeptide.

As used herein, the term "vector" refers to an expression vector capable of expressing a target protein in suitable host cells, and to a gene construct that includes essential regulatory elements to which a gene insert is operably linked in such a manner as to be expressed. The operable linkage to a recombinant vector may be prepared using a genetic recombinant technique that is well known in the art, and site-specific DNA cleavage and ligation may be carried out using enzymes that are generally known in the art. The vector of the present invention may include a signal sequence or a leader sequence for targeting membranes or secretion as well as expression regulatory elements, such as a promoter, an operator, an initiation codon, a stop codon, a polyadenylation signal and an enhancer, and can be constructed in various forms depending on the purpose thereof. The promoter of the vector may be constitutive or inducible. In addition, expression vectors include a selectable marker that allows the selection of host cells containing the vector, and replicable expression vectors include a replication origin. The vector may be self-replicable, or may be integrated into the DNA of a host cell.

Preferably, the vector may further include a tag sequence for protein purification, and examples of the tag sequence for protein purification may include a histidine-tag sequence (His-tag), a HA tag derived from an epitope of the influenza hemagglutinin protein, and a FLAG-tag, and preferably the histidine-tag sequence, but are not limited thereto.

The vector used in the present invention is not particularly limited, as long as it is replicable in the host, and any vector known in the art may be used. The examples thereof may include a plasmid, a viral vector, a phage particle or a simply latent genome insert. When the vector is transformed into an appropriate host, the vector is capable of replicating irrespective of a host genome or being integrated into the host genome.

In one preferred embodiment, the nucleic acid sequence may be codon-optimized to increase its expression in the host cells.

As used herein, the term "codon optimization" refers to the alteration of coding regions of the nucleic acid molecules or codons in the gene to reflect the typical codon usage of the host organism without altering the polypeptide encoded by the DNA. The codon optimization may be carried out by any known technique.

In still another embodiment, the present invention relates to a host cell that is transformed with the vector comprising the fusion polypeptide.

As used herein, the term "transformation" or "transfection" means the introduction of DNA into a host in such a way that it becomes replicable either as an extrachromosomal element or by chromosomal integration. The method of transforming the vector of the present invention may include any method of introducing a nucleic acid into a cell, and may be performed by using suitable standard techniques known in the art, depending on the host cell. Examples thereof include electroporation, calcium phosphate (CaPO$_4$) precipitation, calcium chloride (CaCl$_2$) precipitation, microinjection, a polyethylene glycol (PEG) method, a DEAE-dextran method, a cationic liposome method, and an acetic acid lithium-DMSO method, but are not limited thereto.

The host cells having high introduction efficiency of foreign DNA and having high expression levels of introduced DNA are preferred, and all microorganisms including prokaryotic and eukaryotic cells are possible. The preferred host cell is E. coli, but it is not limited thereto. The E. coli to be used may be selected depending on the type of LRR protein to be fused. For example, if the C-terminus of LRR protein has a disulfide bond, it is efficient to select a strain having an alteration in the E. coli genome-related enzyme for improvement of its expression.

In still another embodiment, the present invention relates to a method for producing a fusion polypeptide with improved solubility and folding, comprising the steps of (a) preparing the vector; (b) introducing the prepared vector into host cells; and (c) recovering the fusion polypeptide from the host cells. In one preferred embodiment, the method may further include the step of (d) purifying the fusion polypeptide using a column.

In still another embodiment, the present invention relates to a method for improving the solubility and folding of the fusion polypeptide, comprising the steps of (a) preparing the vector; (b) introducing the prepared vector into host cells; and (c) expressing the fusion polypeptide in the host cells.

According to one embodiment of the present invention, the present inventors defined the internalin B protein and the repeat modules of VLR protein, and then isolated two consecutive module structures to construct partial structure libraries of internalin B protein and VLR protein. Each module pair were structurally compared through the partial structure library of two proteins, and aligned according to high similarity score to select the module pair containing more sequences of VLR protein itself and less sequences of internalin B protein as the final fusion site. They designed a new fusion protein having the internalin B protein at the N-terminus of the corresponding repeat module pair and the VLR protein sequences at the C-terminus of the corresponding repeat module pair (SEQ ID NOs: 5 and 6). Subsequently, to predict more stable amino acids, the final model structure was determined by Modeller software using the sequence of the binding protein and structure information of the original internalin B protein and VLR protein, and the final sequence candidates altered to have the lowest energy function value were determined using ROSETTADESIGN software (SEQ ID NOs: 7 and 8). DNA was synthesized based on the final designed sequence, and a codon-optimized DNA sequence was synthesized according to the codon preference of *E. coli*. For expression and purification, hexa-histidine residues are linked to the C-terminus of the protein, and transformed into ORIGAMI B *E. coli* to facilitate formation of disulfide bonds contained in the C-terminus of VLR. After purification using His-tag, the production amount was analyzed. As a result, the production was increased by fusion of the N-terminus of internalin, compared to before the fusion (FIG. 9). Further, when DNA was synthesized based on the fusion protein (SEQ ID NOs: 9 and 10) prepared by addition of one consensus module of VLR to the internalin-VLR fusion protein, and expressed in *E. coli*, excessive expression of the soluble protein was maintained (FIG. 12). Soluble expression of the hybrid TV3 protein having the N-terminus from TLR4 and the C-terminus from VLR was increased in *E. coli*, when the VLR repeat module was used as a linker (FIG. 14). These results suggest that the solubility and folding-improved fusion polypeptide can be produced in a large amount, and its solubility and folding can be also improved, when the codon-optimized nucleic acid of the fusion polypeptide is expressed in a suitable *E. coli* host cell.

In still another embodiment, the present invention relates to a method for analyzing the efficacy of the fusion polypeptide, comprising the steps of (a) introducing into an LPS (Lipopolysaccharide) surface receptor-expressing cell line a vector including an expression cassette having a reporter protein-encoding gene operably linked to an NF-κB binding motif-linked promoter and a vector including an expression cassette having a reporter protein-encoding gene operably linked to a promoter devoid of the NF-κB binding motif; (b) mixing in advance MD-2 (Myeloid differentiation protein-2), LPS, and the fusion polypeptides so as to prepare mixtures; (c) contacting the cell line of step (a) with the mixtures prepared in step (b); and (d) determining that the fusion polypeptide of the experimental group has better efficacy than that of the control group, when the experimental group contacted with the fusion polypeptide shows a lower expression level of the reporter gene than the control group not contacted with the fusion polypeptide to be analyzed.

The method of the present invention is preferably a method of screening protein drugs and analyzing their efficacy, based on firefly luciferase. In the method, a firefly luciferase-expressing vector and a Renilla luciferase-expressing vector are simultaneously introduced into HEK293 cells expressing the LPS signal transduction receptor TLR4 and MD-2, and CD14 on the surface, and the activity of firefly luciferase driven by NF-κB activation due to LPS signal transduction is compared to that of Renilla luciferase that is constitutively expressed, thereby analyzing the increased activity by NF-κB. This method of the present invention is shown in the schematic diagram of FIG. 26A.

As used herein, the term "LPS signal transduction receptor" is a receptor required for LPS signal transduction, and is a protein expressed on the cell surface. All receptors are included without limitation, as long as they mediate LPS signal transduction causing sepsis, and examples thereof may include CD14, MD-2, and TLR4.

Figure 27:
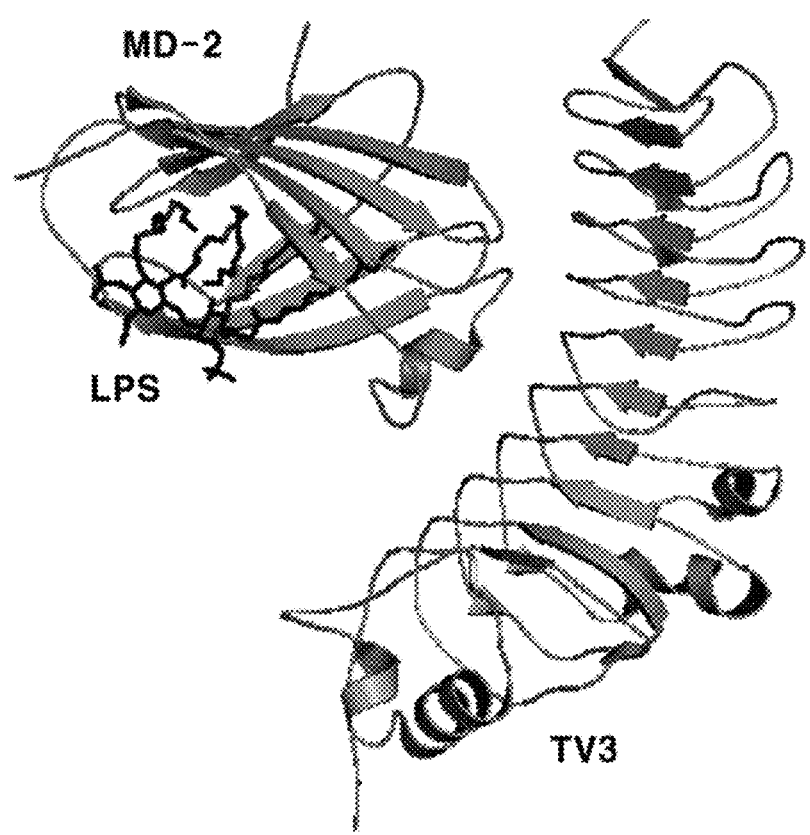
FIG. 27 is the result of X-ray crystallography showing a TV3/MD-2 complex binding with LPS.
Figure 30:
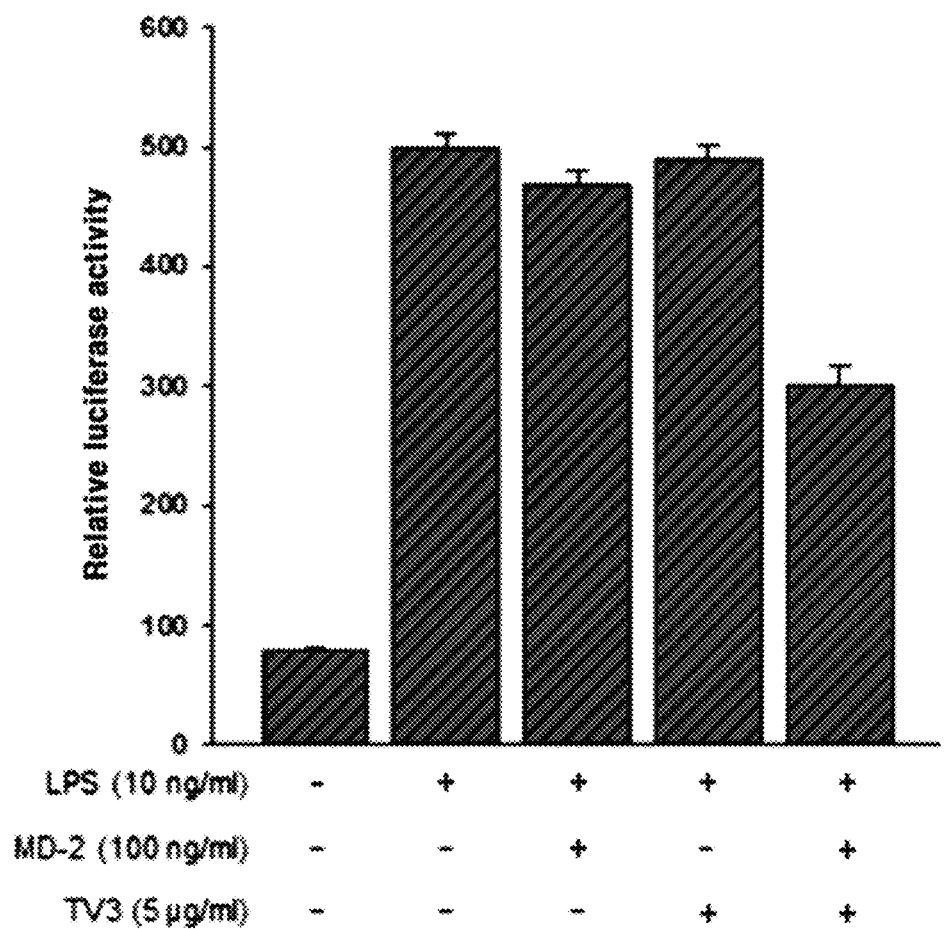
FIG. 30 shows the effect of MD-2 supplied cell-based assay system on the efficacy of protein drugs, in which luciferase vectors were introduced into HEK293 cells expressing TLR4/MD-2/CD14 on the surface.
Figure 32:
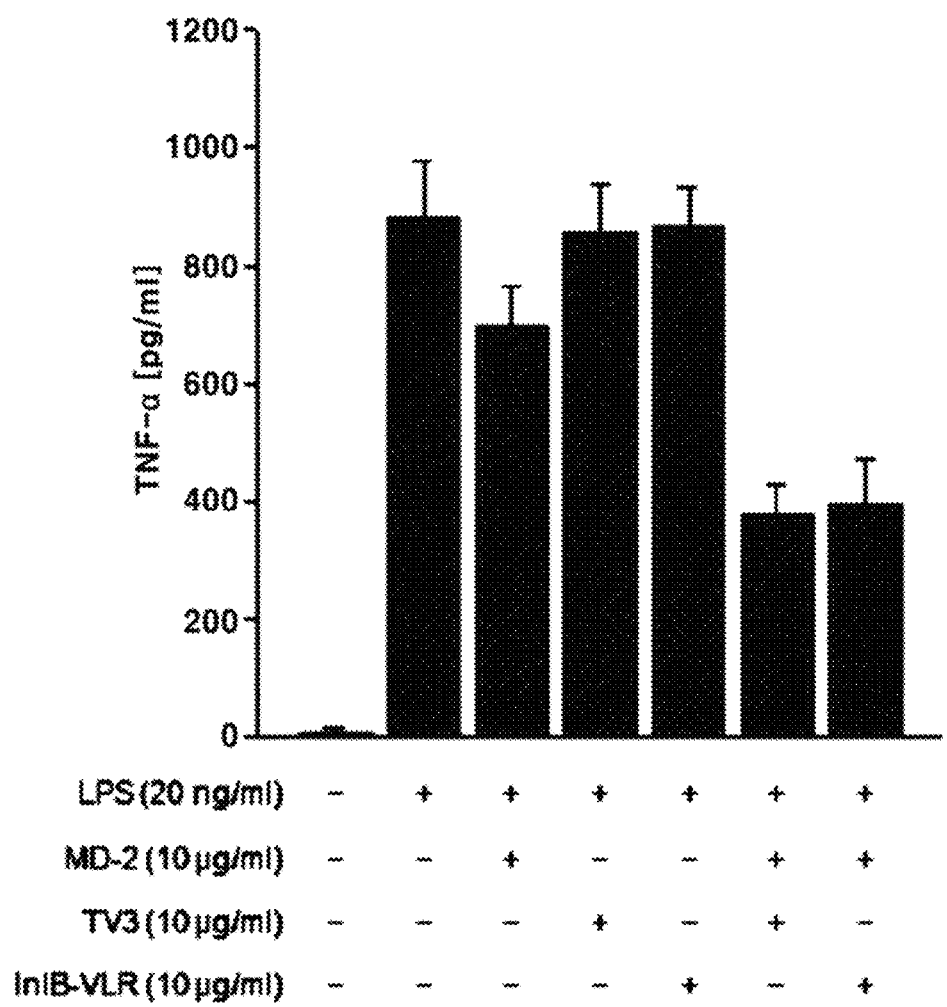
FIG. 32 shows the effect of MD-2 supplied cell-based assay system on the efficacy of protein drugs, in which the amount of TNF-α cytokine released by differentiated THP-1 cells was examined by ELISA.

As used herein, the term "LPS (lipopolysaccharide)" is a macromolecule consisting of a lipid and a polysaccharide joined by a covalent bond, and is the major component of the outer membrane of Gram-negative bacteria. It is also called endotoxin, and is known to induce a strong response from the animal immune system by binding to a TLR4/MD-2 complex among TLRs (Toll-like receptors) involved in innate immunity. That is, excessive LPS signal transduction induces immune hypersensitivity reactions, leading to sepsis. According to one embodiment of the present invention, when the cell-based array system of the present invention provided with the purified MD-2 was used, the sepsis protein drug, fusion polypeptide was found to significantly inhibit LPS signal transduction (FIGS. 30 and 32). This system for screening the therapeutic agents for sepsis or analyzing their efficacy is based on the fact that its accuracy is increased by addition of purified MD-2, together with the protein drugs for sepsis or candidate materials (LRR protein). A binding structure of LPS and the TV3/MD-2 complex, which is a protein drug used in one Example of the present invention, is shown in FIG. 27, and MD-2 binding with TLR4 shows high binding affinity for LPS (Akashi et al., J. Exp. Med., 198(7):1035-1042, 2003). Thus, the purified protein MD-2 is preferably provided for the efficacy analysis on the protein drugs.

As used herein, the term "CD14 (cluster of differentiation 14)" is a protein that is secreted from immune cells or expressed on cell surface, and plays key roles in innate immunity and functions to promote the binding of LPS to the TLR4/MD-2 complex.

As used herein, the term "MD-2 (Myeloid differentiation protein-2)" is, also called lymphocyte antigen 96, a glycoprotein that binds LPS with a binding affinity (Kd) of 65 nM. It forms a complex with TLR4 on the surface of immune cells, and binds with LPS to mediate intracellular signal transduction. That is, it is a protein mediating the interaction between LPS and TLR4.

As used herein, the term "TLR4 (Toll-like receptor 4)" is, also called CD284 (cluster of differentiation 284), one of the TLRs (Toll-like receptors) expressed on the surface of immune cells and involved in innate immunity. TLR4 on the surface of immune cells forms a complex with MD-2, and then forms a complex with LPS via MD-2. Subsequently, the TLR4/MD-2/LPS complex forms a dimer to initiate intracellular signal transduction. LPS signal transduction induces phosphorylation of IκB (inhibitor of NF-κB) binding with NF-κB, and the NF-κB transcription factor released from IκB is then translocated into the nucleus, and involved in transcription of various cytokines, leading to secretion of proinflammatory cytokines. As such, the LPS signal transduction induces the translocation of NF-κB transcription factor into the nucleus. Thus, in one embodiment of the assay system of the present invention, the efficacy of the protein drugs for sepsis can be effectively analyzed using a vector having a promoter linked with NF-κB binding motif.

The cells expressing LPS signal transduction receptors on their surface may be used in the assay system of the present invention without limitation, and preferably a stable cell line of HEK293 cell which is allowed to express all of CD14, MD-2 and TLR4 as LPS receptors for LPS signal transduction. Any cell line suitable for the construction of desirable cell-based assay system of the present invention may be used without limitation, as long as LPS signal transduction is maintained, its stable subculture is possible, and a firefly luciferase reporter gene is easily introduced thereto. Expression of LPS receptors can be achieved by intracellular introduction of vectors capable of expressing each protein. For reproducible experiments, however, a cell line showing a stable expression of CD14 and MD-2, TLR4 is preferably selected. In one Example of the present invention, HEK293/hTLRA-MD2-CD14 (Invivogen, USA) expressing TLR4, CD14 and MD-2 and being stably subcultured was used.

As used herein, the term "NF-κB binding motif" means a motif that binds with NF-κB transcription factor to operate a promoter linked with the motif, leading to expression of downstream genes. In one Example of the present invention, for desirable cell-based assay, a firefly luciferase-expressing vector including "NF-κB binding motif" (Invivogen, USA) and a vector constitutively expressing Renilla luciferase (Promega, USA) are simultaneously introduced into the cells.

In step (a) introducing into an LPS surface receptor-expressing cell line a vector including an expression cassette having a reporter protein-encoding gene operably linked to an NF-κB binding motif-linked promoter and a vector including an expression cassette having a reporter protein-encoding gene operably linked to a promoter devoid of the NF-κB binding motif, the NF-κB binding motif-linked promoter binds with the NF-κB transcription factor that is released from IκB by the LPS signal transduction, leading to expression of the downstream operably linked reporter gene, and the promoter devoid of the NF-κB binding motif induces expression of the downstream operably linked reporter gene irrespective of many other factors including LPS signal transduction (e.g., NF-κB transcription factor, etc.). Preferably, the promoter devoid of the NF-κB binding motif is preferably a HSV-TK promoter, but any promoter known in the art may be used without limitation.

As used herein, the term "operably linked" means that one nucleic acid fragment is linked to another nucleic acid fragment so that the function or expression thereof is affected by the other nucleic acid fragment, but each fragment in the possible combinations of the nucleic acid fragments produces no detectable effect on the function. It means a functional linkage is formed between a regulatory sequence regulating the nucleic acid expression and a nucleic acid sequence encoding the target protein in order to perform the general functions. The operable linkage may be prepared using a genetic recombinant technique that is well known in the art, and site-specific DNA cleavage and ligation may be carried out using enzymes that are generally known in the art.

Figure 28:
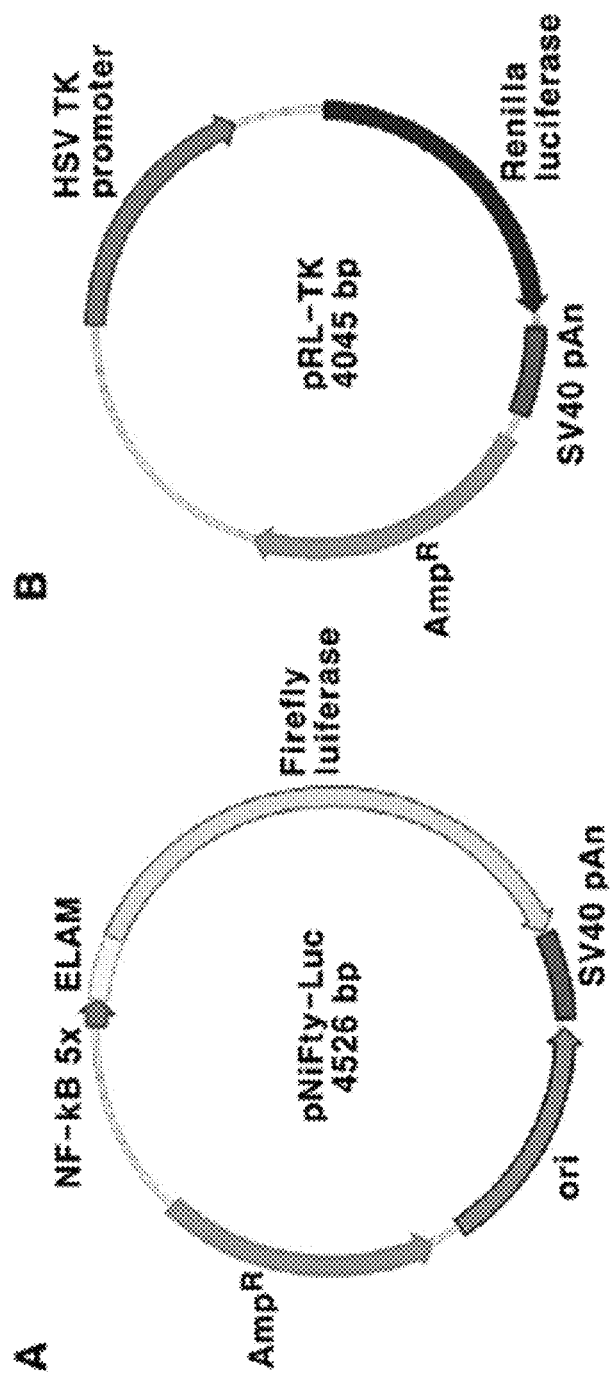
FIG. 28 shows cleavage maps of firefly luciferase reporter-expressing vector (Invivogen) induced by NF-κB activation due to LPS signal transduction and Renilla luciferase-expressing internal standard vector (Promega), in which A is cleavage map of firefly luciferase reporter-expressing vector, B is cleavage map of Renilla luciferase-expressing internal standard vector.

The reporter proteins of step (a) are different from each other, and may include a variety of distinguishable reporter proteins. Examples thereof may include, but are not limited to, green fluorescent protein (GFP), CAT (CM acetyl transferase), β-galactosidase, SEAP (secreted alkaline phosphatase), firefly luciferase, and Renilla luciferase, and preferably, firefly luciferase and Renilla luciferase. According to one preferred embodiment of the present invention, a vector having a firefly luciferase-encoding gene operably linked to an NF-κB binding motif-linked promoter (FIG. 28A) and a vector having a Renilla luciferase-encoding gene operably linked to a HSV-TK promoter devoid of the NF-κB binding motif (FIG. 28B) were used. The vector having a Renilla luciferase-encoding gene operably linked to the HSV-TK promoter is constitutively expressed irrespective of LPS signal transduction, and thus suitably used as a control group of firefly luciferase.

As used herein, the term "introduction" means introduction of a foreign DNA into a host cell by transformation or transfection. The transformation may be performed by various methods known in the art such as calcium chloride ($CaCl_2$) precipitation, a Hanahan method that is an improved $CaCl_2$ method by using DMSO (dimethyl sulfoxide) as a reducing material, electroporation, calcium phosphate ($CaPO_4$) precipitation, protoplast fusion, agitation using silicon carbide fiber, Agrobacterium-mediated transformation, polyethylene glycol (PEG)-mediated transformation, dextran sulfate-, microinjection, LIPOFECTAMINE-, and desiccation/inhibition-mediated transformation. Transfection means the delivery of a gene into a cell using a virus or viral particle by means of infection.

According to one embodiment of the present invention, cell lines treated with each vector of step (a) showed relatively reduced luciferase activity by treatment of an LPS inhibitor polymyxin B and an LPS antagonist LPS-RS (FIGS. 29A and 29B), suggesting that the cell lines of the present invention are suitable for an efficacy test of LPS inhibitors, namely, therapeutic agents for sepsis.

As used herein, the term "fusion polypeptide" as used in the efficacy test is a protein that is provided for disturbing immune responses by binding of LPS to the TLR4/MD-2 complex on the surface of immune cells. The fusion polypeptide binds to MD-2 that forms an insoluble complex, when it exists alone, and maintains the MD-2 structure suitable for LPS binding. It may include TV3 protein prepared by hybrid LRR technique, or hybrid LRR proteins prepared by fusion of LRR protein fragments similar to TLR4, but is not limited thereto. Preferably, it may be a fusion polypeptide prepared by fusion of the N-terminus of internalin B protein, modified repeat modules of VLR (Variable Lymphocyte Receptor) protein, and the C-terminus of VLR protein. This protein drug may be selected from LRR proteins or a sequence mutation library, prepared by combinations of LRR repeat modules, and the drug candidates for sepsis can be also selected in the similar way.

The efficacy test of the fusion polypeptides of the present invention as a therapeutic agent for sepsis may be performed by (b) mixing in advance MD-2, LPS, and the fusion polypeptides to be analyzed; contacting the cell line of step (a) with the prepared mixtures; and determining whether the fusion polypeptide of the experimental group has better efficacy than that of the control group, when the experimental group contacted with the fusion polypeptide shows a lower expression level of the reporter gene than the control group not contacted with the fusion polypeptide to be analyzed. That is, the experimental group is contacted with the mixture of MD-2, LPS and a fusion polypeptide to be analyzed, and the control group is contacted with the mixture of MD-2, LPS and the fusion polypeptide other than that of the experimental group. This efficacy test can be used to analyze the functions between the selected fusion polypeptides and to determine whether the known protein drugs for sepsis practically block the LPS signal transduction.

In step (d) determining whether the fusion polypeptide of the experimental group has an excellent function as a protein drug for sepsis, when the experimental group contacted with the fusion polypeptide and MD-2 showed a lower expression level of the reporter gene than the control group not contacted with the fusion polypeptide to be analyzed, the values (relative luminescence value) obtained by dividing the luminescence value of the reporter protein operably linked to the NF-κB binding motif-linked promoter by that of the reporter protein operably linked to the promoter devoid of the NF-κB binding motif were compared. When the experimental group has a lower value than the control group, the fusion polypeptide can be determined to have excellent efficacy.

The method of the present invention can be used to analyze the efficacy of the protein drug for sepsis by comparing the relative expression levels of reporter proteins between the known protein drug and the fusion polypeptide.

In still another embodiment, the present invention provides a method for analyzing the efficacy of the fusion polypeptide, comprising the steps of (a) differentiating THP-1 cell line using PMA (phorbol 12-myristate 13-acetate); (b) mixing in advance MD-2 (Myeloid differentiation protein-2), LPS, and the fusion polypeptides as protein drugs for sepsis so as to prepare mixtures; (c) contacting the cell line of step (a) with the prepared mixtures of step (b); and (d) determining whether the fusion polypeptide of the experimental group has better efficacy than that of the control group, when the experimental group contacted with the fusion polypeptide shows a lower TNF-α level than the control group not contacted with the fusion polypeptide to be analyzed.

Figure 26:
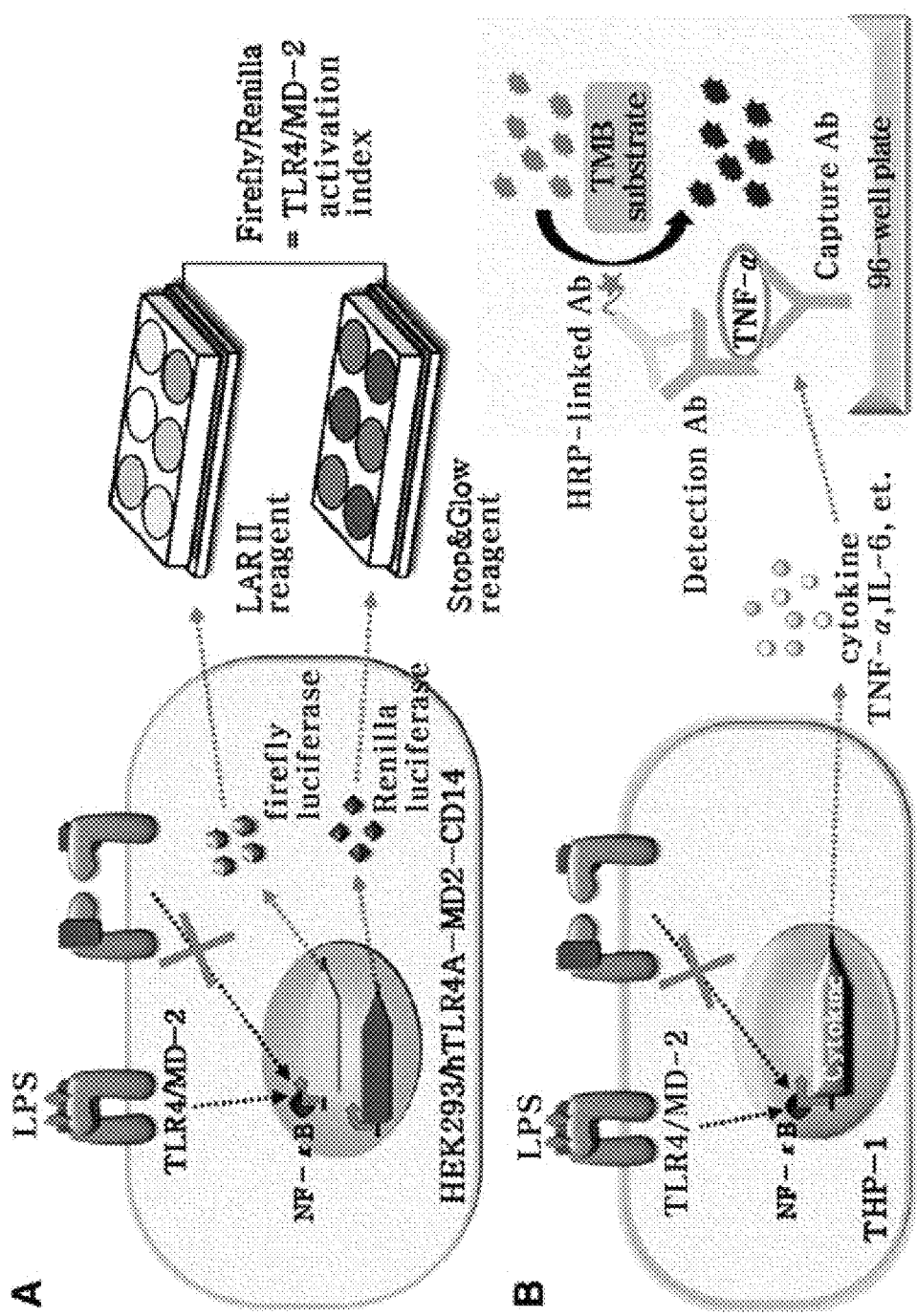
FIG. 26 shows LPS signal transduction and a cell-based assay for analyzing efficacy of the protein drugs according to the present invention, in which A is a cell-based assay for analyzing efficacy of the protein drugs using luciferase reporter, and B is an immune cell-based assay for analyzing efficacy of the protein drugs by ELISA of TNF-α.

This method using THP-1 of the present invention is shown in the schematic diagram of FIG. 26B.

With respect to the objects of the present invention, TNF-α may be replaced with cytokines, of which expression is increased by the binding of NF-κB transcription factor due to LPS signal transduction.

As used herein, the term "THP-1" is a cell line, having characteristics of a human monocyte-derived macrophage, widely used in immunocytochemical analysis. Its long-term subculture is possible and it is easily differentiated into macrophage by PMA (phorbol 12-myristate 13-acetate) or vitamin D3. In particular, THP-1 is frequently used as a monocyte cell model expressing LPS receptor proteins on the surface, suitable for the construction of the desirable cell-based assay system of the present invention.

The TNF-α secretion of step (d) may be analyzed by any method of analyzing a protein expression level known in the art without limitation, and preferably it may be analyzed by measuring the secretion amount of TNF-α in a medium using ELISA (Enzyme-Linked Immunosorbent Assay).

According to one embodiment of the present invention, when THP-1 cells differentiated using PMA were treated with an LPS inhibitor polymyxin B, a reduction in TNF-α secretion was observed (FIG. 31), suggesting that the THP-1 cell line of the present invention is a cell line suitable for the efficacy test of LPS inhibitors, namely, therapeutic agents for sepsis. In addition, treatment of fusion polypeptide and MD-2 significantly reduced the TNF-α secretion (FIG. 32), suggesting that the cell line and the assay system of the present invention can be used for the efficacy test of therapeutic agents for sepsis. Therefore, the present invention provides a method for analyzing the efficacy of a therapeutic agent for sepsis, the fusion polypeptide, by using the cell line and MD-2.

MODE FOR INVENTION

Hereinafter, the present invention will be described in more detail with reference to Examples. However, these Examples are for illustrative purposes only, and the invention is not intended to be limited by these Examples, and various modifications and changes may be made thereto.

Example 1

Preparation of Internalin-VLR Fusion Protein and its High Expression in E. coli

<1-1> Design and Preparation of Internalin-VLR Fusion Protein

The *Listeria monocytogenes*-derived internalin B protein and the hagfish-derived VLR protein variant were used as the components of the present invention. The VLR protein (SEQ ID NO: 2 and FIG. 2) was prepared to have 5 repeat modules by deleting the N-terminal signal sequence region and the C-terminal stalk region, based on the structure of Eb8VLRB.59 having three repeat modules (SEQ ID NO: 1 and FIG. 1) and by adding two other naturally occurring other module sequences. The purpose of increasing the number of modules is to investigate the possibility of variations in the number of modules.

The other scaffold (SEQ ID NO: 3 and FIG. 3) was designed to have 5 repeat modules by consensus design selecting evolutionarily conserved amino acids from numerous VLR protein sequences. At this time, those having 5 repeat modules prepared as above (SEQ ID NO: 2 and FIG. 2) were used for the N-terminus and C-terminus. As shown in SEQ ID NO: 3, 18 amino acids of 24 amino acids present in one module are evolutionarily conserved, and variable amino acids are assigned in the other 6 amino acids according to evolutionary conservation. 15 amino acids in two scaffold sequences were modified for binding with other proteins (modified amino acids are underlined in SEQ ID NO: 2 of FIG. 2, and the same positions are underlined in SEQ ID NOs: 3 to 7).

To bind the N-terminus of internalin B protein to the VLR protein, the most probable binding site was identified. Two proteins are leucine rich proteins, but there are differences in the module length and the pattern of repeat modules involved in structural stability. Thus, for its minimal effect, a method of identifying binding sites was developed.

First, the repeat modules of each protein were defined, and then two consecutive module structures were isolated to construct partial structure libraries of leucine rich protein. Considering only the internal repeat module excluding N- and C-terminus, partial structures of 6 module pairs of 7 repeat modules in the internalin B protein, and 5 module pairs of total 6 modules consisting of 5 repeat modules and 1 VLRe module in the VLR protein were prepared. Strictly, the VLRe module is a C-terminal component, but it partly maintains the repeat sequence having 24 amino acids as the same in the repeat modules, thereby being selected as a fusion candidate. Each of the module pairs was divided into Inl1~Inl6, VLRn1~VLRn5, and VLRc1~VLRc5 according to the order from the N-terminus. The constructed partial structure libraries of two proteins were used to perform comparison between the structures of the pairs (total 30 pairs). Finally, the pair having the highest similarity was selected and combined. As shown in the following Table 1, a pair of Inl4 and VLRn5 showed the highest similarity score (Alignment score) of 20, among the module pairs selected as candidates. In this regard, the similarity between the partial structures was defined as follows: structure alignment of the hydrophobic residues involved in maintenance of protein stability was performed, followed by alignment of other sequences, and then evolutionary relationships (BLOSUM62) of the paired amino acids were converted as scores.

Among the module pairs aligned by similarity, the module pair of internalin 2 and VLR 1, which contains more sequences of VLR protein itself and less sequences of internalin B protein, was determined as the final fusion site, because this fusion is made to increase the expression level while maintaining the known LRR characteristics.

TABLE 1

<Similarity analysis between internalin protein and VLR protein module>

| InlB | VLRn | Similarity score | InlB | VLRc | Similarity score |
|---|---|---|---|---|---|
| 4 | 5 | 20 | 2 | 2 | 23 |
| 5 | 3 | 18 | 2 | 1 | 18 |
| 6 | 3 | 15 | 4 | 5 | 12 |
| 6 | 4 | 14 | 5 | 3 | 11 |
| 2 | 1 | 13 | 6 | 4 | 11 |
| 2 | 2 | 12 | 1 | 1 | 10 |
| 5 | 1 | 12 | 6 | 3 | 9 |

The identified partial structure pair can be determined as a consecutive repeat module pair showing the highest similarity between the internalin B protein and the VLR protein, and thus structure alignment of two proteins was performed based on this module pair. Then, a novel binding protein was designed by locating the internalin B protein and the VLR protein at the left (N-terminal direction) and right (C-terminal direction) of the corresponding repeat module pair, respectively (SEQ ID NOs: 5 and 6, and FIGS. 4 and 5).

Figure 8:
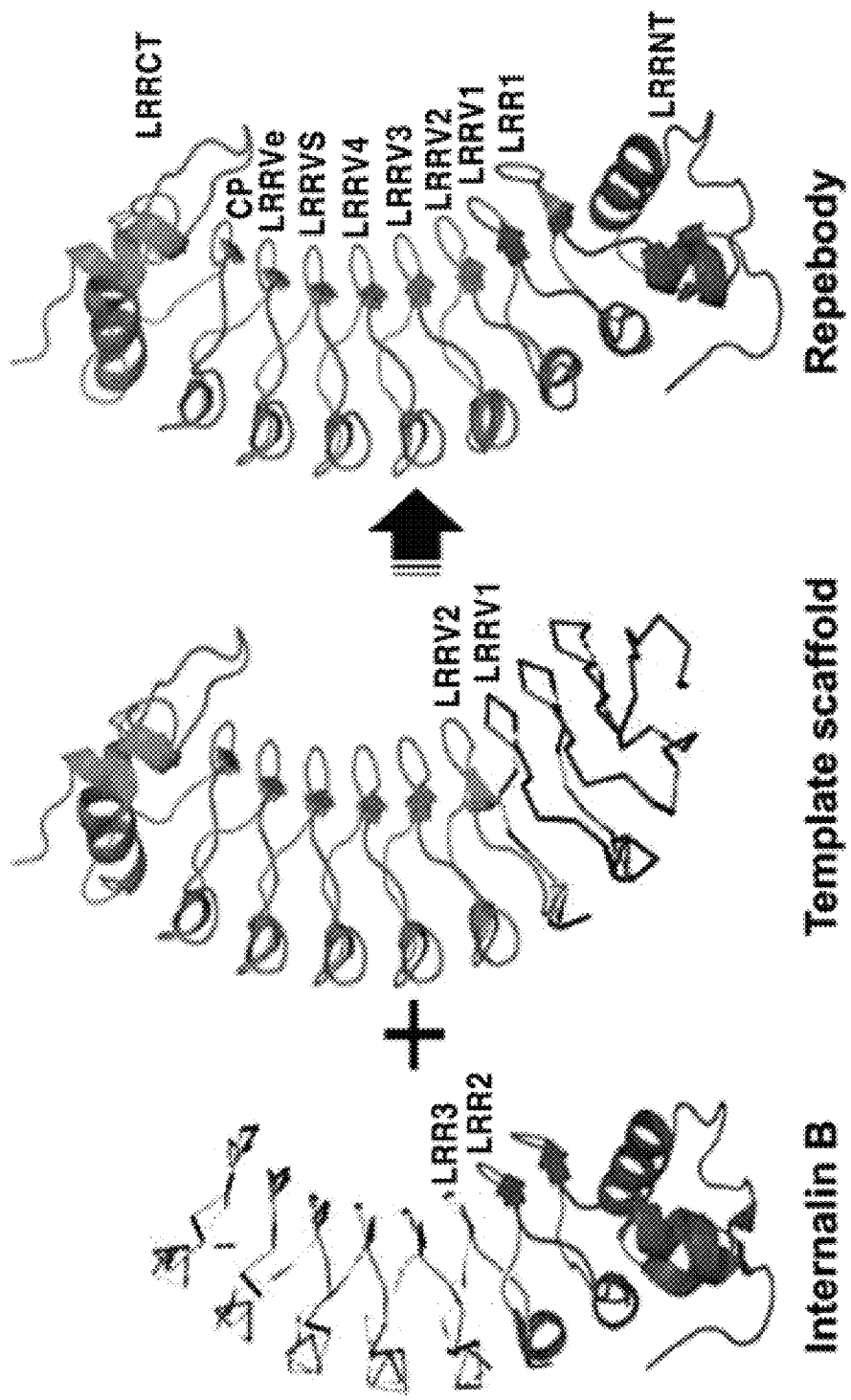
FIG. 8 is a schematic diagram showing a method of fusing internalin B protein for the production of LRR protein of the present invention in E. coli.

To predict more stable amino acids, the final model structure was determined by Modeller software (version 9v4) using the sequence of fusion protein and structure information of original internalin B protein and VLR protein. During this process, an initial model structure was first constructed using the automodel function of Modeller software. To optimize the initial structure, the molecular dynamics simulation and energy stabilization process were repeated (using the slow_large optimization protocol of Modeller). Consequently, a final model structure showing a stable connection between the internalin B protein and the VLR protein was identified. The module of internalin B protein located at the fusion site of the different proteins was redesigned considering its interaction with the neighboring VLR protein module. 12 appropriate amino acid residues were selected to perform the redesigning using the ROSETTADESIGN program, in which the hydrophobic residues involved in maintenance of protein stability and evolutionary conserved residues were fixed and other hydrophilic residues of the protein surface were modified. The altered residues correspond to x in the module pattern of internalin B protein (LpxLxxLxLxxxNxIxDIxxLxx; SEQ ID NO:13 from amino acid 62 to 83). During the sequence designing process of the ROSETTADESIGN program, optimal residues were searched using the fixed backbone model with MC minimization for each rotamer search. 100 candidates were selected by 100 independent simulations, and the candidate having the lowest energy function value was determined as the final candidate (SEQ ID NOs: 7 and 8, FIGS. 6 and 7). The method of designing the internalin-VLR fusion protein is shown in the schematic diagram of FIG. 8.

<1-2> High Expression of Soluble Fusion Protein in E. coli

DNA was synthesized based on the amino acid sequence (SEQ ID NOs: 7 and 8, FIGS. 6 and 7) finally designed in Example <1-1>. The DNA sequence did not comply with the known DNA sequence of *Listeria* or hagfish, and was newly synthesized according to the codon preference of *E. coli*. The synthesized DNA was cloned into pET21a vector (Qiagen) with a hexa-histidine tag at the C-terminus in order to facilitate the expression and purification thereof. The cloned vector was transformed into ORIGAMI B *E. coli* (Novagen) to enhance disulfide bond formation in the C-terminus of VLR. The *E. coli* cells transformed with the vector were grown until the absorbance (OD600) reached 0.5. IPTG (Isopropyl β-D-1-thiogalactopyranoside) was then added at a final concentration of 0.5 mM, and the cells were further incubated at 18° C. for 20 hours for production of the internalin-VLR fusion protein. After 20 hours, cells were disrupted, and the amounts of internalin-VLR fusion protein produced in the cells were compared. The original protein showing a lower production amount was purified using the His-tag through a Ni-NTA resin and concentrated followed by analysis.

Figure 9:
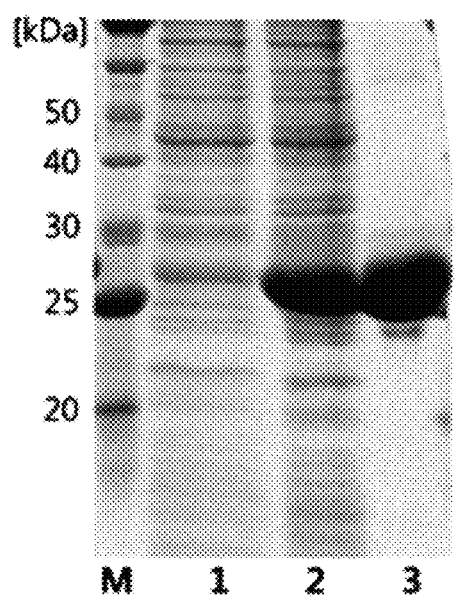
FIG. 9 is the result of polyacrylamide electrophoresis showing that production of the internalin-VLR fusion protein designed by the present invention was increased, compared to the VLR protein alone, in which pET21a was used as a vector, ORIGAMI B was used as a host cell and cultured in 5 ml of LB medium, protein expression was induced by IPTG (final 0.5 mM), and the resulting protein purified by Ni-NTA resin was expressed, and when expression levels were compared between before and after purification, a remarkable difference was observed. M: size marker, 1: VLR proteins (before purification), 2: VLR proteins fused with internalin proteins (before purification), 3: VLR proteins fused with internalin proteins (after purification)

As a result, as shown in FIG. 9, production of the fusion protein was greatly increased, compared to before the fusion with the N-terminus of internalin. After internalin fusion, the production amount was 10 mg per 100 ml of culture, suggesting that the internalin-LRR fusion protein by the method of the present invention can be produced in a large amount in a soluble form.

Example 2

Design of Internalin-VLR Fusion Protein with Additional Repeat Module and its Expression <2-1> Design of Internalin-VLR Fusion Protein with Additional Repeat Module In order to use the internalin-VLR fusion protein as a binding protein for disease target proteins that are various in type and size, it is required to modulate the number of repeat modules for adjustment of the binding area. An experiment designing a protein with one additional repeat module was performed to determine whether the N-terminus of internalin stably expresses the VLR protein when protein mutation for a larger binding area is induced by addition of a repeat module.

Based on SEQ ID NOs: 7 and 8, which are the internalin-fused scaffold prepared in Example <1-1>, one additional VLR consensus module was added next to the internalin to design SEQ ID NOs: 9 and 10 (FIGS. 10 and 11).

<2-2> High Soluble Expression of Fusion Protein with Additional Repeat Module in *E. coli*

DNA was synthesized based on SEQ ID NOs: 9 and 10 prepared in Example <2-1>, and expressed in *E. coli* in the same manner as in Example <1-2>.

Figure 12:
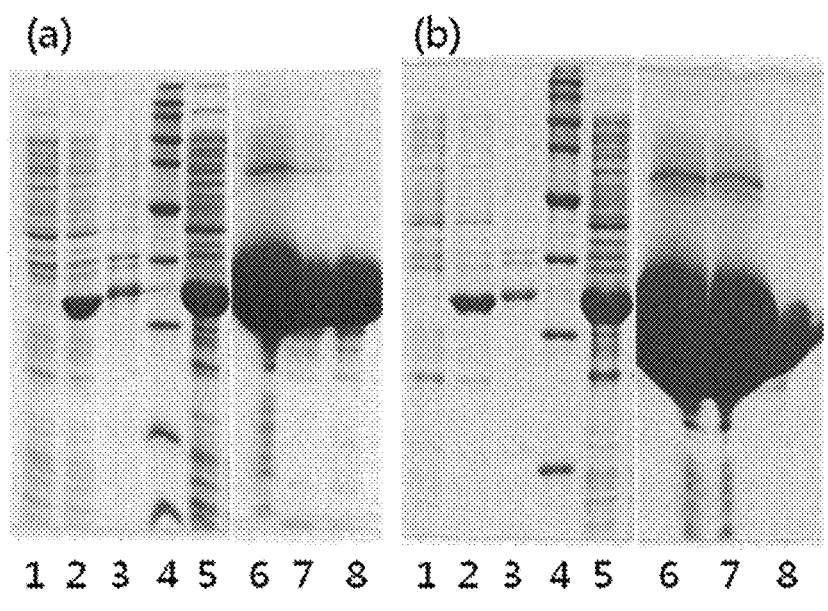
FIG. 12 is the result of polyacrylamide electrophoresis showing the expression level of internalin-VLR fusion protein having the addition of one repeat module, in which (a) represents the expression level of InlB-VLR6n, (b) represents the expression level of InlB-VLR6c fusion protein, total protein levels under uninduced (1) and induced (2) conditions were compared to determine the expression level, expression levels of insoluble (3) and soluble (5) proteins were compared to determine the expression level of soluble protein, and high expression of soluble protein was observed, 1: total protein under uninduced conditions, 2: total protein under induced conditions, 3: insoluble protein, 4: size marker, 5: soluble protein, 6 to 8: fractions after protein purification.
Figure 14:
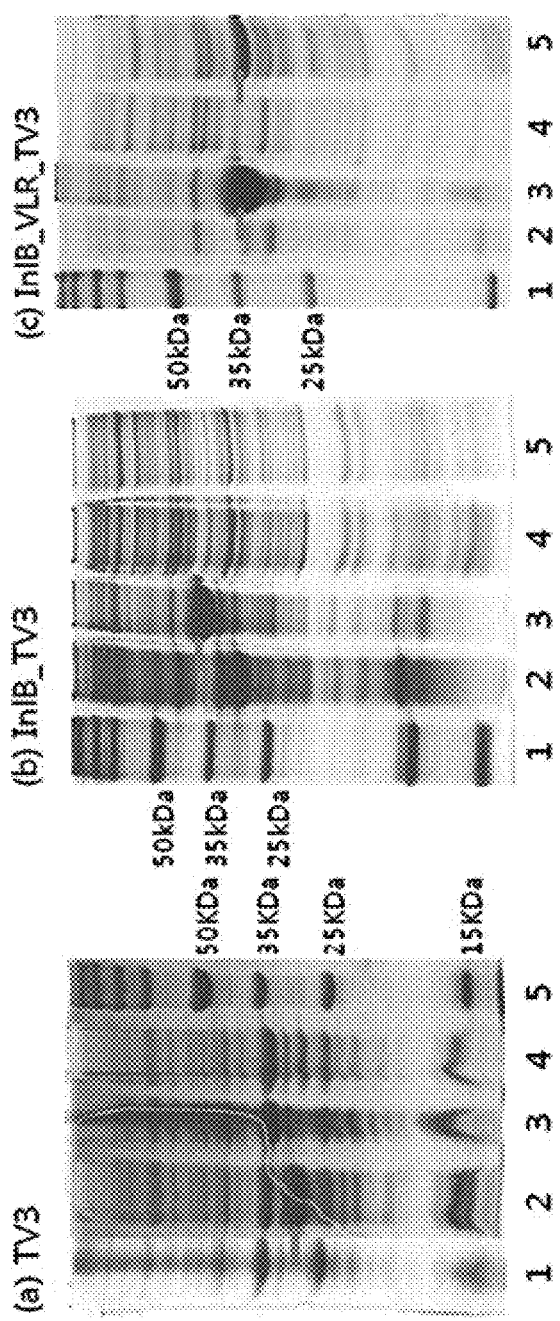
FIG. 14 is the result of polyacrylamide electrophoresis showing increased expression level of soluble form of the fusion protein that is prepared by linking internalin with VLR using a linker, in which (a) 1: TV3 insoluble region-uninduced, 2: TV3 insoluble region-induced, 3: TV3 soluble region-uninduced, 4: TV3 soluble region-induced, 5: size marker; (b) 1: size marker, 2: InlB_TV3 insoluble region-uninduced, 3: InlB_TV3 insoluble region-induced, 4: InlB_TV3 soluble region-uninduced, 5: InlB_TV3 soluble region-induced; (c) 1: size marker, 2: InlB_VLR_TV3 insoluble region-uninduced, 3: InlB_VLR_TV3 insoluble region-induced, 4: InlB_VLR_TV3 soluble region-uninduced, 5: InlB_VLR_TV3 soluble region-induced.

As a result, highly soluble expression was observed (FIG. 12). The production amount was 20 mg per 1 L of culture. These results suggest that the increase in the number of the VLR repeat modules in the fusion protein of the present invention does not affect its high expression, indicating the fusion protein of the present invention and the production method thereof can be used for the development of therapeutic agents capable of binding to target proteins of various diseases.

Example 3

Preparation of Internalin-TV3 Fusion Protein and Soluble Expression in *E. coli*

<3-1> Design of Internalin-TV3 Fusion Protein

In order to examine whether the N-terminus of internalin is applied to other LRR family proteins, an internalin-TV3 fusion protein was designed. TV3 protein is synthesized by fusion to reveal the protein structure of one of the LRR proteins, TLR4 (Toll-like receptor-4), and is prepared by fusion of the N-terminus from TLR4 and the C-terminus from VLR. This protein was used to obtain the protein tertiary structure by expression in insect cells. There is a difficulty in low production yields, and in that it is expressed in *E. coli* in an insoluble form only.

The present inventors performed an experiment for the development of a linker module used for the fusion site of the N-terminus of internalin protein and TV3.

The repeat modules of TV3 protein consist of 24 or more amino acids, whereas those of internalin protein consist of 22 amino acids. Therefore, there are differences in the positions of the hydrophobic residues involved in maintenance of protein stability between the two repeat modules, and these differences may disturb stable protein production. In order to overcome this problem, the internalin and the VLR fusion protein designed by the method of Example <1-1> were used in terms of structural stability, because the VLR protein consists of 24 repeat modules like TV3 protein, and was expressed well by binding with the internalin protein. Thus, linking the N-terminus of internalin containing one additional VLR protein module to the N-terminal repeat modules (24) of TV3 protein was attempted. It was expected that this method would maintain the structural stability in binding of repeat modules having different sizes and increase the expression level of the fusion protein.

From the sequences of the internalin protein and the VLR fusion protein designed by the method of Example <1-1> (SEQ ID NO: 8, FIG. 7), the sequences (24 amino acids) spanning from the N-terminal sequence of internalin to the repeat modules of the VLR protein were determined to bind with the region of TV3 protein (24 amino acids) which maintains its original sequence and has the same size with the repeat modules of the VLR protein. That is, 53-100 regions of TV3 protein were determined as two consecutive partial structures as in Example <1-1>, and aligned in the fusion site of the internalin-VLR fusion structure to construct an initial binding structure model. Then, a new sequence was designed by locating internalin-VLR (1 module) at the left (N-terminus) and TV3 (76-end) at the right (C-terminus) of the alignment. A stable model structure was obtained using Modeller software in the same manner as in Example <1-1>. In addition, the amino acids of the fusion site, inconsistent with the consensus information, were replaced with the consensus sequences by sequence optimization. That is, the consensus information includes highly conserved amino acid information in the corresponding site by evolutionary analysis. Based on the information, hydrophobic amino acids involved in protein stability were replaced with the consensus sequences (SEQ ID NO: 12 and FIG. 13, replaced residues underlined). During this procedure, the ROSETTADESIGN software program was used as in Example <1-1>, and optimization of hydrophilic residues was not performed and the consensus information only was used. One repeat module of VLR protein inserted in the middle of fusion protein functions as a linker, and plays a role of tightly linking between the N-terminus of internalin protein and the TV3 protein. Consequently, the internalin-LRR fusion protein linked via the linker protein was designed.

<3-2> Soluble Expression of Internalin-TV3 Fusion Protein Via Linker Module in E. coli Since the TV3 DNA sequence has t-RNA codon lacking in E. coli, protein was expressed using ROSETTA-GAMI B (Novagen) *E. coli* supplying the corresponding tRNA. The expression method is the same as in Example <1-2>, except that ROSETTA-GAMI B (Novagen) was used as *E. coli*.

As a result, a soluble protein was produced, unlike the internalin protein before fusion (FIG. 14). Compared to the known protein that could not be obtained in a soluble form, there was a great enhancement in the expression of solubility, and approximately 6 mg of pure protein was obtained per 1 L of culture broth. One repeat module of VLR protein inserted in the middle of the fusion protein functioned as a linker, and plays an important role of tightly linking between the N-terminus of internalin protein and the TV3 protein. When no linker was used, the internalin-TV3 fusion protein was not expressed as the soluble form, as shown in FIG. 4. These results suggest that the soluble protein can be produced in a large amount by designing the fusion protein using the linker.

Example 4

Design of Amino Acids Binding to MD-2 Protein Using Internalin-Fused VLR Scaffold Protein and Measurement of Binding Affinity Thereof <4-1> Selection of Internalin-Fused VLR Scaffold Protein (IVLR) and Amino Acid Design to Mimic TV3-MD2 Interaction A scaffold named IVLRn was used as a component. This scaffold is a protein prepared by fusion of the N-terminus and the first repeat module of *Listeria monocytogenes*-derived internalin B protein and four repeat modules and subsequent C-terminus of naturally occurring VLR protein, and is represented by SEQ ID NO: 14 (FIG. 20).

TV3 protein was prepared by fusion of a part of human TLR-4 receptor interacting with MD-2 and a part of VLR protein introduced for stability enhancement (Cell, 2007, 130, 906-917), and TV3 is known to have an affinity of $7.6\times10^{-8}$ M as it is. Its tertiary structure was revealed by X-ray crystallography. Amino acids involved in the interaction were determined by the distance between two proteins (within 4.5 Å), and the corresponding amino acids of TV3 were Q39, M41, E42, D60, S62, F63, D84, S86, R87, T110, V132, V134, E135, N156, H159, S183, D209, S211, L212, W256, Q284.

The present inventors constructed IVLRn-MD2 (SEQ ID NO: 15 and FIG. 21) capable of binding with MD-2 by mutation of the corresponding amino acid residues of IVLRn with the amino acids of TV3 involved in the interaction.

<4-2> Soluble Expression of Designed Protein in *E. coli* and Measurement of Binding Affinity for MD-2

DNA was synthesized based on the amino acid sequence (SEQ ID NO: 15) finally designed in Example <4-1>. The DNA sequence did not comply with the known DNA sequence of *Listeria* or hagfish, and was newly synthesized according to the codon preference of *E. coli*. The synthesized DNA was cloned into pET21a vector (Qiagen) with a hexa-histidine tag at the C-terminus in order to facilitate the expression and purification. The cloned vector was transformed into ORIGAMI B *E. coli* (Novagen) to enhance disulfide bond formation in the C-terminus of VLR. The *E. coli* cells transformed with the vector were grown until the absorbance (OD600) reached 0.5. IPTG (Isopropyl β-D-1-thiogalactopyranoside) was then added at a final concentration of 0.5 mM, and the cells were further incubated at 18° C. for 20 hours for production of the internalin-VLR fusion protein. After 20 hours, cells were disrupted, and the production amounts of internalin-VLR fusion protein in the cells were compared. The original protein showing a lower production amount was purified using the His-tag through a Ni-NTA resin, and concentrated, followed by analysis.

MD-2 protein was produced using a protein expression vector in insect cells, and purified. The protein A gene was cloned into pAcGp67 vector for purification of MD-2 and protein, and then expressed in an insect cell system using baculovirus. The expressed protein released from Hi5 insect cell line was isolated and purified using a IgG SEPHAROSE affinity resin, and then the protein A was removed from MD-2 by thrombin cleavage, followed by further purification by ion exchange chromatography and gel filtration.

The binding affinity between the two proteins was measured by SPR (Surface Plasmon Resonance) using a BIACORE 3000 system. The produced IVLRn-MD2 was fixed on a BIACORE CM5 chip by EDC/NHS reaction using sodium acetate buffer at pH 4. The level of immobilized protein was approximately 500 to 800 RU (resonance units). Various concentrations of MD-2 were injected using HSB-EP buffer, and sensorgram data were obtained (FIG. 18). Signals in the sensorgrams were subtracted from a mock reference cell to minimize the effect of nonspecific binding, and the binding affinity $K_D$ was determined using BIACORE Evaluation software.

As a result, the binding affinity between IVLRn-MD-2 and MD-2 was $4.15\times10^{-8}$ M, which is similar to that between TV3 and MD-2 (FIG. 18).

Example 5

Consensus-Designed Internalin-Fused VLR Scaffold Protein Binding to MD-2 Protein and Measurement of Binding Affinity Thereof <5-1> Consensus-Designed Internalin-VRL Fusion Protein and Design Thereof for Binding to MD-2

Consensus information can be obtained by amino acid frequency and replacement information of each sequence position from the evolutionary associated sequences. Evolutionarily, amino acids involved in structure formation and stability or sequence positions involved in interaction are highly conserved, whereas relatively frequent replacements are observed in other sequences showing no effect on structural stability. Consensus information allows the definition of amino acids to be replaced at each position, based on the type and frequency of amino acids at the corresponding position. Therefore, such evolutionary analysis increases the possibility of designing various sequences with structural stability.

An advantage of VLR in the consensus analysis is the high modularity of repeat modules because VLR variation is generated by recombination, like antibodies. The phenylalanine spine of VLR forms a hydrophobic core together with 4 surrounding leucines, and this structure was expected to increase stability.

Sequences for consensus design were collected from Uniprot DB and NCBI database, and nr databases by using a BLAST search. Sequences were collected from UniProt DB using the keywords VLR and leucine, and 100 VLR sequences were also obtained from the NCBI and nr database by using a BLAST search to one protein sequence (PDB ID: 2O6Q). For selection of repeat modules, a motif consisting of 24 amino acids was obtained using a typical LRR motif (Typical LRR motif: LxxLxxLxLxxNxLxxLxxxxFxx; SEQ ID NO:22).

Alignment score was obtained using the typical LRR motif, and a sequence having the alignment score of 39 or higher was selected. From the resulting sequences, 765 (Uniprot) and 500 (NCBI nr) were used. Logo plot was used for consensus definition. In Logo plot, a distinct conserved region was used as it is, and amino acids contributing to the structural stability were selected for a mutated region.

The results are as follows.
Consensus sequence
1) Uniprot DB LTNLTxLxLxxNQLKSLPxGVFDN (SEQ ID NO:23)
2) NCBI nr LTKLTxLxLxxNQLQSLPxGVFDK (SEQ ID NO:24)
underlined: highly conserved region
in bold: moderately conserved region
x: mutated region The sequences suitable for a moderately conserved region (in bold) were selected based on the following two criteria; 1) amino acid frequency, 2) uncharged amino acids.

The reason for selecting uncharged amino acids is to prevent crowding of charged amino acids of repeat modules at one position. Finally, the sequence "LTNLxxLxLxxN-QLQSLPxGVFDK" (SEQ ID NO: 19 from amino acid 132 to 155) was determined as the consensus module, wherein x is an evolutionary variable region, and the binding affinity and specificity for target proteins are determined by the type of amino acids at this region. In the consensus module consisting of 24 amino acids, x represents any amino acid. As IVLRn in Example 5, it was designed to have 4 VLR repeat modules, named IVLRc (SEQ ID NO: 19 and FIG. 25).

Amino acids involved in the binding with MD-2 were replaced into the corresponding region, as in Example 4. Naturally occurring VLR amino acids were selected for the mutated region x, which is not involved in the binding, and it was named IVLRc-MD2 (SEQ ID NO: 16 and FIG. 22).

<5-2> Expression of Designed Protein and Analysis of Binding Affinity

DNA was synthesized based on SEQ ID NO: 16 prepared in Example <5-1>, and expressed in *E. coli* in the same manner as in Example <4-2> to measure its binding affinity for MD-2 protein.

As a result, its binding affinity, $K_D$ value was $6.21 \times 10^{-8}$ M, which is similar to those of TV3-MD-2 and IVLRn-MD-2. The protein expression level was 60 mg/L, which was greatly increased, compared to the previous fusion with internalin (3 mg/L). The stability (melting temperature (Tm) measured by circular dichroism) of IVLRn-MD2 and IVLRc-MD2 was 70° C. and 83° C. These results suggest that the novel protein of the present invention showed remarkably increased expression levels compared to the known protein, and consensus design can be also applied to improve the protein characteristics as a therapeutic agent.

Example 6

Inhibitory Effect of IVLRc-MD2 Protein on Intracellular LPS Signal Transduction and Therapeutic Effect Thereof on Sepsis <6-1> Production of IVLRc-MD2 Protein and Removal of Endotoxin The IVLRc-MD2 protein was produced and purified in the same manner as in Example <4-2>. Purification of the protein is required for experiments at a cell or animal level. However, a large amount of endotoxin is problematically released from *E. coli* during the protein purification in a biological experiment, unlike experiments for physicochemical properties. LPS, one of polysaccharide expressed on the cell surface of Gram negative bacteria, causes biological effects such as inflammation even though it exists at a very small amount. Therefore, it is necessary to remove endotoxin from *E. coli* for the prevention of toxicity in a practical experiment. Unfortunately, a large amount of LPS is also obtained during the protein purification. The obtained LPS causes unwanted biological response, resulting in negative influence on experimental results. To overcome this problem, the present inventors packed a column with an LPS-specific polymyxin-B-agarose resin (Sigma, Cat#p1441-10ML) for effective LPS removal, and then applied the solution containing LPS and protein to the column, and eluted only the desirable protein using a PBS buffer solution. The LPS content during initial protein purification was >30,000 EU/ml, and the final LPS content was reduced to 12.8 EU/ml (3.2 EU/mg protein), and used for further experiment.

<6-2> Development of Cell-Based Assay System for Monitoring MD-2 Inhibitory Effect and Assay of IVLRc-MD2 Function Using the Same In order to examine whether the InlB-VLR fusion protein binds with MD-2 to show inhibitory effect on LPS signal transduction as a form of InlB-VLR/MD-2 complex, the following experiment was performed. A complex of MD-2 and sTLR4 consisting of a soluble extracellular domain of a cell membrane receptor TLR4 has an ability of capturing LPS, and thus shows inhibitory effects on LPS signal transduction via a TLR4 receptor on the cell membrane. It is known to have a competitive inhibitory effect of sTLR4/MD-2 complex with wtTLR4/MD-2 complex on a cell membrane (Mitsuzawa et al., J. Immunolo., 177:8133-8139, 2006; Brandl et al., J. Endotoxin Res., 11:197-206, 2005). Therefore, the present inventors performed the following experiment in order to examine the competitive inhibitory effect of InlB-VLR/MD-2 complex on LPS signal transduction in the same mechanism as the inhibition of sTLR4/MD-2 complex on LPS.

First, THP-1 monocyte (TIB-202TM, ATCC) was cultured in RPMI containing 10% FBS (Fetal Bovine Serum) and 50 UM 2-mercaptoethanol at 37° C. and 5% CO2. When cell density reached 90%, they were washed with a DPBS buffer solution (pH 7.4). Then, to increase the sensitivity to LPS, the cells were suspended in a medium supplemented with 200 nM PMA (phorbol 12-myristate-13-acetate), and aliquoted to a 96-well plate in a density of $2.5\times10^4$/well, followed by incubation for 72 hours at 37° C. and 5% CO2 for differentiation.

Prior to the experiment, 10 µg/ml of InlB-VLR and MD-2-added RPMI medium, and 10 µg/ml of MD-2 and 10 µg/ml of IVLR-added medium, 10 µg/ml of TV3-added medium, and 10 µg/ml of TV-3 and MD-2-added medium as control groups were prepared and left at 37° C. for 1 hour. Then, THP-1 differentiated into macrophage by PMA was washed with DPBS buffer solution (pH 7.4) three times, and the sample-containing RPMI media were treated with 20 ng/ml of LPS and THP-1, followed by incubation at 37° C. and 5% CO2 for 6 hours. After 6 hours, a predetermined amount of culture was taken from each well, and diluted 4-8 fold using DPBS buffer solution (pH 7.4), followed by ELISA (Enzyme-Linked Immunosorbent Assays) for the secreted TNF-α.

Figure 16:
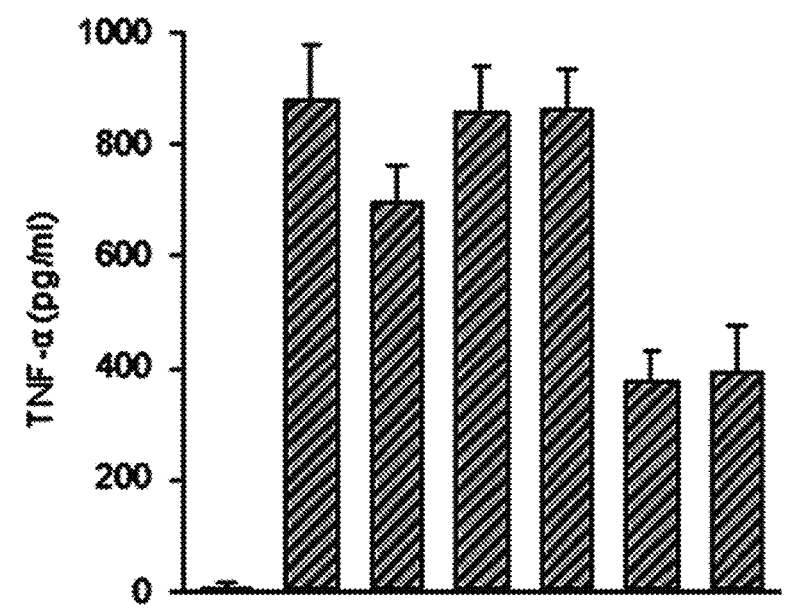
FIG. 16 shows the blocking effect of IVLRc/MD-2 complex on sepsis-related signal transduction caused by LPS and MD-2, in which the effect was similar to that of the known TV3 (at this time, the effect can be observed by a mixture of protein and MD-2)

The results are shown in FIG. 16. As shown in FIG. 16, InlB-VLR/MD-2 complex and TV3/MD-2 complex inhibited LPS signal transduction to greatly reduce the TNF-α secretion by 50%. On the contrary, when InlB-VLR and TV3 were used alone, there was no inhibitory effect on LPS signal transduction. When MD-2 was used alone, a weak inhibitory effect was observed (Mitsuzawa et al., J. Immunolo., 177:8133-8139, 2006). Meanwhile, InlB-VLR/MD-2 complex and TV3/MD-2 complex showed almost similar inhibitory effects on LPS signal transduction, suggesting that it is the same as the inhibitory effect on LPS signal transduction by binding of sTLR4 or TV3 with MD-2 (Mitsuzawa et al., J. Immunolo., 177:8133-8139, 2006; Jung et al., PLoS ONE, 4:e7403, 2009). These results demonstrate that the InlB-VLR fusion protein of the present invention binds with MD-2 to inhibit LPS signal transduction in the form of InlB-VLR/MD-2 complex, suggesting that the novel MD-2-binding polypeptide of the present invention can be used as a therapeutic agent for sepsis.

Example 7

Addition of Module to IVLRc-MD2 Protein and its Binding Effect

In Examples <4-2> and <5-2>, the binding affinities of the prepared proteins for MD-2 were demonstrated. However, the present inventors designed a new protein by improving the binding affinity or properties of the protein based on the IVLR scaffold. First, one additional repeat module and amino acids capable of binding to the added module were added, and the amino acids of the fused internalin module that can affect the binding were also replaced so as to design new proteins, IVLRn5-MD2 and IVLRc5-MD2 (SEQ ID NOs: 17 and 18, FIGS. 23 and 24). The designed proteins were expressed and purified in the same manner as in Example <4-2>, and their binding affinity and stability were measured.

As shown in FIG. 19, the result of pull-down assay using GPC (Gel Permeation Chromatography) showed that all of the new IVLR proteins bind to MD-2 protein, respectively. These results suggest that the scaffold proteins can be applied to various fields by variation in the number of modules of IVLR protein, while their binding affinity for the target protein, MD-2, is maintained.

The melting temperature of IVLRc5-MD-2 measured by CD (Circular Dichroism) was 8412, and there was little difference in the melting temperature between IVLRc5-MD-2 and IVLRc-MD2 (83° C.). However, IVLRn5-MD-2 had the melting temperature of 77° C., which is 5° C. higher than IVLRn-MD-2. These results suggest that the protein property can be improved without negative effect on the binding affinity, and thus the IVLR scaffold protein can be used in the designing and preparation of more excellent proteins for practical and industrial use.

Example 8

Construction of Cell-Based Assay Using HEK293 Cell Expressing TLR4 and MD-2, CD14 on Surface and Luciferase Reporters The present inventors constructed a system capable of monitoring activation of TLR4-MD-2 receptor by LPS using a firefly luciferase-expressing vector, pNiFty-Luc (Invivogen) and a Renilla luciferase-expressing vector, pRL-TK (Promega) as a control group, as shown in FIG. 26A. In the firefly luciferase-expressing vector (pNiFty-Luc) used in the present invention, the NF-κB binding site exists on the promoter region to initiate luciferase gene expression by LPS signal transduction (FIG. 28A). In addition, expression of Renilla luciferase-expressing vector (pRL-TK) is maintained by HSV-TK promoter that is not affected by many other factors including LPS signal transduction, and thus is suitable as the control group for the firefly luciferase-expressing vector (FIG. 28B).

<8-1> Preparation of HEK293 Model Cell and Expression Vector

In order to monitor activation of TLR4-MD-2 receptor by LPS, an HEK293/hTLR4A-MD2-CD14 cell line (Invivogen) stably expressing TLR4 and MD2, CD14 genes, prepared by introduction of the genes into HEK293 cell, was used. The HEK293/hTLR4A-MD2-CD14 cell line was subcultured in an RPMI medium (Invitrogen) supplemented with 10% Fetal Bovine Serum (FBS) in an incubator at 37° C. and 5% $CO_2$, and then used for the experiment.

In addition, two luciferase-expressing vectors used in the present invention were prepared in the endotoxin-removed form from DH5a strains that were transformed with the vectors using an ENDOFREE Plasmid Maxi Kit (QIAGEN).

<8-2> Preparation of LPS Inhibitor and Antagonist, and Protein Drugs

In the present invention, the LPS inhibitor, polymyxin B (Invivogen) and the LPS antagonist, LPS-RS (Invivogen) were diluted in RPMI media at a concentration of 0.01-100 μg/ml, and reacted with 10 ng/ml of LPS at 37° C. for 1 hour. The protein drugs of Example 7 were prepared in RPMI media with 5 μg/ml of TV3 and 100 ng/ml of MD-2, 10 ng/ml of LPS, and the control groups were prepared in RPMI media with 5 μg/ml of TV3 and LPS, and 100 ng/in of MD-2 and LPS, followed by incubation at 37° C. for 1 hour.

<8-3> Luciferase Reporter Assay

The luciferase reporter vectors were introduced into HEK293/hTLR4A-MD2-CD14 cell using Lipofectamin™ 2000 (Invitrogen) as follows:

First, HEK293/hTLR4A-MD2-CD14 cell was cultured in a T-25 flask at 37° C. and 5% $CO_2$, until the cells reached 90% confluence. Then, the cells were treated with trypsin-EDTA, and detached from the bottom of the flask, and plated in a 24-well plate at a density of $2\times10^5$ cell/well, followed by incubation at 37° C. and 5% $CO_2$. After 24 hours, the pNifty-Luc vector and the pRL-TK vector were introduced into the cells using Lipofectamin™ 2000 at the same time. After 4 hours, the media were replaced with RPMI media supplemented with 10% serum, followed by incubation at 37° C. and 5% $CO_2$ for one day. On the next day, the media were removed from the 24-well plate, and then RPMI media containing the LPS inhibitor and antagonist or the protein drugs together with LPS prepared in Example <8-2> were added to cells, followed by incubation at 37° C. and 5% $CO_2$. After 6 hours, activation of firefly luciferase by LPS signal transduction was examined using a DUAL-LU-CIFERASE Reporter Assay System (Promega) as follows:

First, the media were removed from the 24-well plate, and the plate was washed with a PBS buffer solution twice, and then 200 µl of passive lysis buffer (PLB) was added to each well for cell lysis. After 30 minutes, 20 µl of cell lysate was transferred to a new 96 well-plate, and then 100 µl of LAR II reagent containing a substrate of firefly luciferase was added to measure luminescence using a VICTOR X Multi-label Plate Reader (PerkinElmer) for 0.5 seconds. After measurement of firefly luciferase luminescence, 100 µl of STOP & GLO reagent containing a substrate of Renilla luciferase was added to measure Renilla luciferase luminescence for 0.5 second. That is, this method is a relative analysis method, in which the luciferase?expressing vector and the Renilla luciferase-expressing vector as a control group were simultaneously introduced into HEK293 cell expressing the LPS receptor, TLR4 and MD-2, and CD14 on the surface, and the luminescence of firefly luciferase initiated by NF-κB activation due to LPS signal transduction was compared to that of Renilla luciferase (FIG. 26A).

Figure 29:
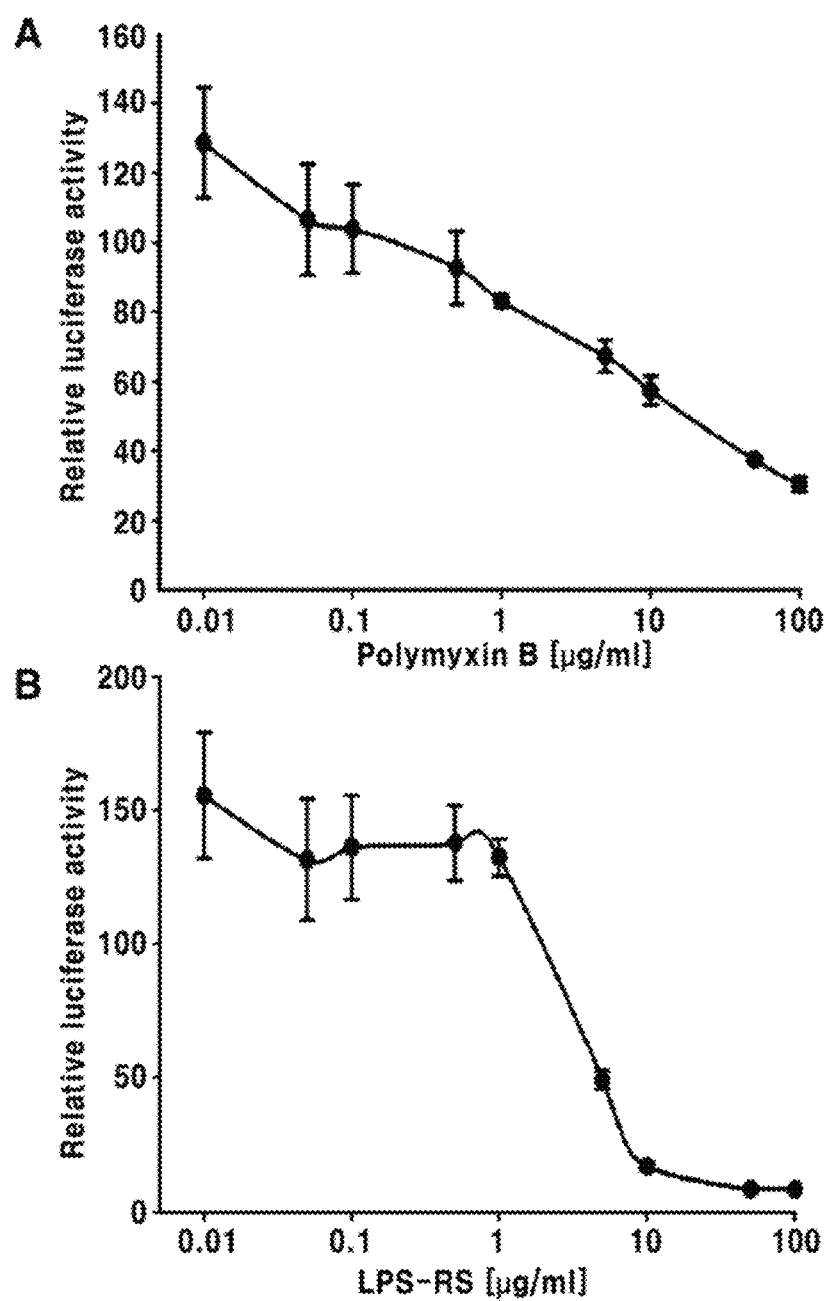
FIG. 29 shows the validity of the cell-based assay system, in which luciferase vectors were introduced into HEK293 cells expressing TLR4/MD-2/CD14 on the surface, and the blocking effects by LPS inhibitor or antagonist were examined, A is the inhibitory effect of Polymyxin B on LPS signal transduction, B is the inhibitory effect of LPS-RS on LPS signal transduction.

The luminescence value of firefly luciferase was divided by that of Renilla luciferase and used as an index of TLR4/MD-2 receptor activation by LPS. According to this method, the reduction in LPS signal transduction by increasing concentration of the LPS inhibitor polymyxin B was determined by a relative reduction of firefly luciferase activity (FIG. 29A). Similarly, the reduction in LPS signal transduction by increasing concentration of the LPS antagonist LPS-RS was determined by a relative reduction of firefly luciferase activity (FIG. 29B).

These results support that the assay system of the present invention can be used for accurate analysis of the signal transduction-blocking effect by LPS inhibitor or antagonist.

Under the same conditions, the LPS signal transduction-blocking effect of the protein drugs provided by the present invention was analyzed. As a result, the inhibitory effect was significantly increased by treatment of both TV3 and MD-2, compared to treatment of LPS and TV3, or MD-2 alone (FIG. 30).

These results support that the assay system provided with MD-2 can be used for stably analyzing the efficacy of therapeutic agents for sepsis.

Example 9

Construction of Cell-Based Assay Monitoring TNF-α Cytokine Secretion Level of Differentiated THP-1 by ELISA The present inventors constructed a cell-based assay method for monitoring cytokine TNF-α secretion level by LPS signal transduction using ELISA (FIG. 26B) and the leukemia patient-derived monocyte THP-1 easily differentiated into macrophage by PMA (phorbol 12-myristate 13-acetate) or vitamin D3, as follows:

<9-1> Cultivation and Preparation of THP-1 Cell

Monocyte THP-1 (TIB-202TM, ATCC) was cultured in RPMI media supplemented with 10% Fetal Bovine Serum (FBS) and 50 UM of 2-mercaptoethanol at 37° C. and 5% $CO_2$. When the cells reached 90% confluence, they were washed with PBS buffer solution (pH 7.4). In order to increase LPS sensitivity, the cells were suspended in RPMI media containing 200 nM of PMA (phorbol 12-myristate-13-acetate), and plated in a 96-well plate at a density of $2.5 \times 10^4$ cells/well, and differentiated at 37° C. and 5% CO2 for 72 hours.

<9-2> Construction of Determination Method of Cytokine Secretion Level of THP-1 by ELISA Prior to the experiment, the LPS inhibitor polymyxin B was diluted in RPMI at a concentration of 1-100 µg/ml, and incubated at 37° C. for 1 hour. In addition, 10 µg/ml of TV3 and MD-2 together with LPS were added to RPMI medium, 10 µg/ml of InlB-VLR and MD-2 together with LPS were added to RPMI medium, and each 10 µg/ml of InlB-VLR, TV3, and MD-2 were singly added to RPMI media. The prepared RPMI media was incubated at 37° C. for 1 hour. Then, THP-1 cells differentiated into macrophages by PMA were washed with a PBS buffer solution (pH 7.4) three times, and RPMI media containing the protein drugs and control groups or control groups were treated to THP-1, together with 20 ng/ml of LPS, followed by incubation at 37° C. and 5% $CO_2$. After 6 hours, a predetermined amount of culture was taken from each well, and diluted 4-8 fold using a PBS buffer solution (pH 7.4), followed by typical ELISA (Enzyme-Linked Immunosorbent Assays, ebioscience) for the secreted TNF-α. The results were calculated from a standard curve of TNF-α.

Figure 31:
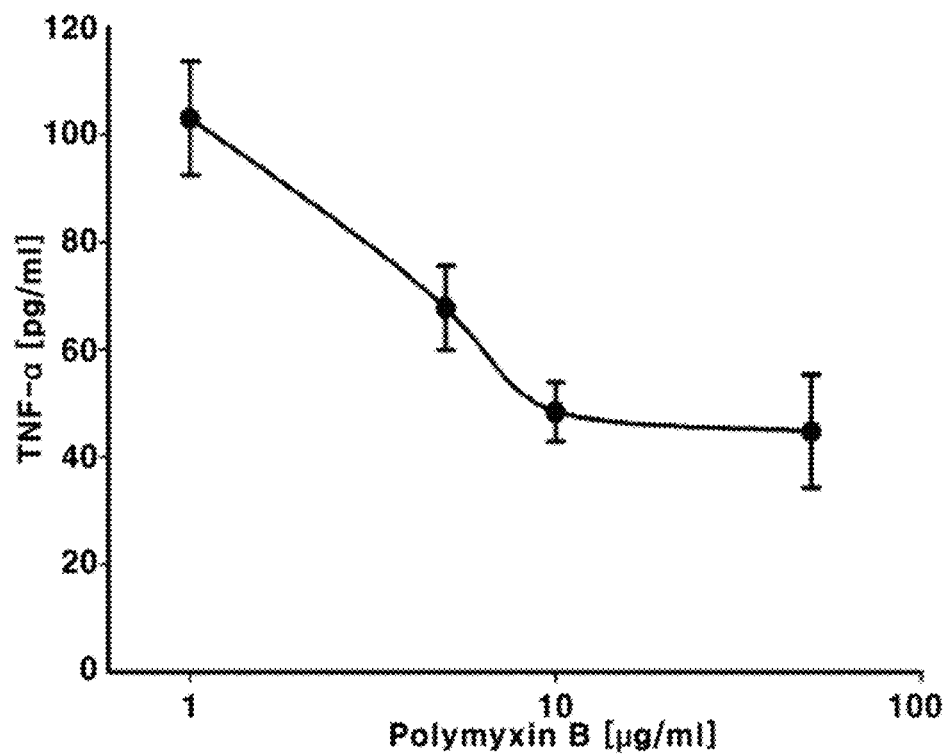
FIG. 31 shows the validity of the cell-based assay system, in which THP-1 cells differentiated by treatment of PMA were treated with a LPS inhibitor polymyxin B, and the amount of TNF-α cytokine released to media was examined by ELISA.

As a result, a reduction in LPS signal transduction according to the concentration of LPS inhibitor polymyxin B was observed (FIG. 31). Under the same conditions, the inhibitory effects of the protein drugs on LPS signal transduction were examined. The inhibitory effects were significantly increased by treatment of TV3 and MD-2, or InlB-VLR and MD-2, compared to treatment of LPS and TV3, or MD-2 alone (FIG. 32).

These results support that the assay system provided with MD-2 can be used to more accurately analyze the efficacy of the protein drug that is a soluble fusion polypeptide prepared by fusion of internalin and LRR family protein.

The invention claimed is:

1. A water-soluble fusion polypeptide prepared by fusion of the N-terminal domain of internalin protein, and LRR (Leucine-rich repeat) family protein,
wherein the fusion polypeptide has an amino acid sequence selected from the group consisting of SEQ ID NO:7, 8, 9, 10, 12, 15, 16, 17 and 18.

2. A method for analyzing the efficacy of the soluble fusion polypeptide of claim 1, comprising the steps of:
   (a) differentiating THP-1 cell line using PMA (phorbol 12-myristate 13-acetate);
   (b) mixing in advance MD-2 (Myeloid differentiation protein-2), LPS (lipopolysaccharide), and the soluble fusion polypeptides of claim 1 so as to prepare mixtures;
   (c) contacting the cell line of step (a) with the prepared mixtures of step (b); and
   (d) determining that the soluble fusion polypeptide of claim 1 of the experimental group has better efficacy than that of the control group, when the experimental group contacted with the soluble fusion polypeptide of claim 1 shows a lower TNF-α (tumor necrosis factor alpha) level than the control group not contacted with the soluble fusion polypeptide of claim 1 to be analyzed.

* * * * *